(12) United States Patent
Bruce et al.

(10) Patent No.: US 10,376,213 B2
(45) Date of Patent: Aug. 13, 2019

(54) SYSTEM, METHOD AND APPARATUS FOR SENSOR INSERTION

(75) Inventors: Robert Bruce, Beaverton, OR (US);
David Kreitlow, Aloha, OR (US);
Isaac Federiuk, Tigard, OR (US);
Ryan Polcin, Somerset, WI (US);
Dennis Slomski, Tualatin, OR (US);
Eric Ward, Portland, OR (US); Mihai Resch, Beaverton, OR (US)

(73) Assignee: WAVEFORM TECHNOLOGIES, INC., Salem, NH (US)

( * ) Notice: Subject to any disclaimer, the term of this patent is extended or adjusted under 35 U.S.C. 154(b) by 1552 days.

(21) Appl. No.: 12/495,238

(22) Filed: Jun. 30, 2009

(65) Prior Publication Data

US 2010/0331642 A1    Dec. 30, 2010

(51) Int. Cl.
*A61B 5/05* (2006.01)
*A61B 5/00* (2006.01)
*A61B 5/145* (2006.01)
*A61B 17/34* (2006.01)

(52) U.S. Cl.
CPC ........ *A61B 5/6846* (2013.01); *A61B 5/14532* (2013.01); *A61B 17/3468* (2013.01)

(58) Field of Classification Search
CPC . A61B 5/14532; A61B 5/1455; A61B 5/1459; A61B 5/0448; A61B 5/443; A61B 5/14555; A61B 5/0059; A61B 5/14551; A61B 5/1495; A61B 5/14552; A61B 5/02154; A61B 5/1464; A61B 5/4266; A61B 5/14542; A61B 5/14539; A61B 5/4362; A61B 5/0408; A61B 18/1492; A61B 19/201; A61F 9/00736; A61M 2025/0031; A61M 5/1582; A61M 39/0208
USPC ....................................................... 600/345
See application file for complete search history.

(56) References Cited

U.S. PATENT DOCUMENTS

| 5,165,407 | A | 11/1992 | Wilson et al. |
| 5,299,571 | A | 4/1994 | Mastrototaro |
| 5,586,553 | A | 12/1996 | Halili et al. |
| 5,931,814 | A | 8/1999 | Alex et al. |

(Continued)

FOREIGN PATENT DOCUMENTS

| CN | 101304697 | 11/2008 |
| JP | 2006-501878 | 1/2006 |

(Continued)

*Primary Examiner* — Patricia Mallari
*Assistant Examiner* — Michael A Catina
(74) *Attorney, Agent, or Firm* — Schwabe Williamson & Wyatt, PC

(57) ABSTRACT

Embodiments provide a sensor insertion tool (SIT) that provides a motive force for insertion of an analyte sensor into/through skin. A SIT may be releasably locked to one or more components of a sensor insertion system, such that components of the sensor insertion system remain securely coupled during sensor insertion. A SIT may include a release member that unlocks or uncouples the SIT and the other components after sensor insertion. In various embodiments, a SIT may be a component of a sensor insertion system configured for assembly by an end user, a health care professional, and/or a caretaker prior to sensor insertion, and may act in cooperation with other sensor insertion system components. Additional components and methods of assembly and use are also provided herein.

15 Claims, 16 Drawing Sheets

(56) References Cited

U.S. PATENT DOCUMENTS

| | | | |
|---|---|---|---|
| 5,954,643 | A | 9/1999 | VanAntwerp et al. |
| 5,965,380 | A | 10/1999 | Heller et al. |
| 6,093,172 | A | 7/2000 | Funderburk et al. |
| 6,501,976 | B1 | 12/2002 | Sohrab |
| 6,565,509 | B1 | 5/2003 | Say et al. |
| 6,676,630 | B2 | 1/2004 | Landau et al. |
| 6,695,860 | B1 | 2/2004 | Ward et al. |
| 6,699,218 | B2 | 3/2004 | Flaherty et al. |
| 2007/0173706 | A1* | 7/2007 | Neinast et al. .............. 600/309 |
| 2007/0249992 | A1* | 10/2007 | Bardy ................ A61B 17/3468 604/60 |
| 2008/0139903 | A1 | 6/2008 | Bruce et al. |
| 2008/0161656 | A1 | 7/2008 | Bruce et al. |
| 2008/0188731 | A1 | 8/2008 | Brister et al. |
| 2008/0319414 | A1 | 12/2008 | Yodfat et al. |
| 2009/0062767 | A1 | 3/2009 | Van Antwerp et al. |
| 2009/0234212 | A1* | 9/2009 | Slomski ................ A61B 5/6849 600/345 |

FOREIGN PATENT DOCUMENTS

| | | |
|---|---|---|
| JP | 2008-506468 | 3/2008 |
| MX | 2010010104 | 2/2011 |
| WO | 2007058921 | 5/2007 |
| WO | 2008083379 | 7/2008 |
| WO | 2009032588 | 3/2009 |
| WO | 2009117452 | 9/2009 |

\* cited by examiner

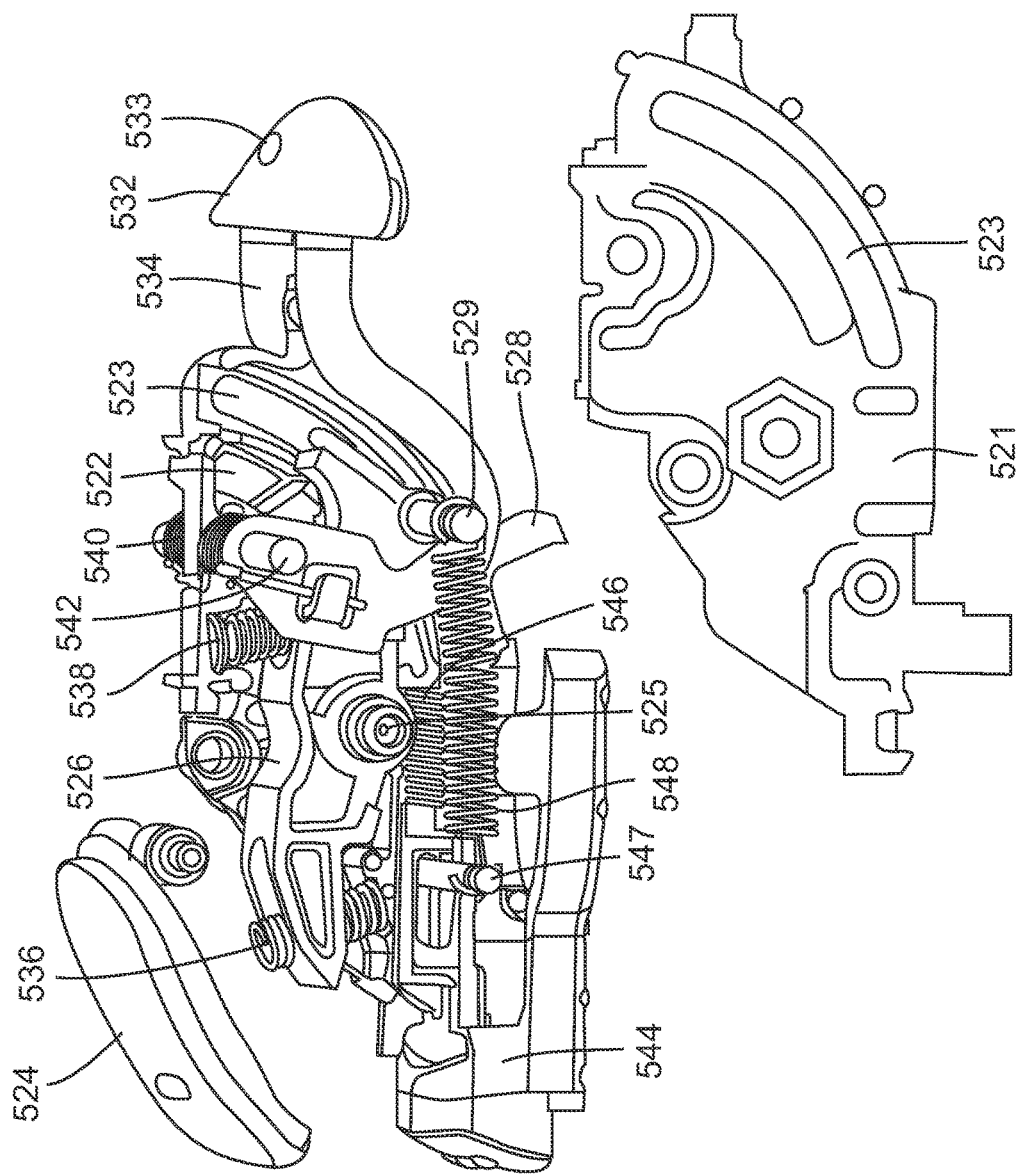

SYSTEM, METHOD AND APPARATUS FOR SENSOR INSERTION

CROSS REFERENCE TO RELATED APPLICATIONS

The present application is related to U.S. Patent Application No. 61/037,246, filed Mar. 17, 2008, entitled "Analyte Sensor Subassembly and Methods and Apparatuses for Inserting an Analyte Sensor Associated with Same," the entire disclosure of which is hereby incorporated by reference in its entirety.

TECHNICAL FIELD

Embodiments herein relate to devices for inserting analyte sensors into a subject, and, more specifically, to a sensor insertion tool for insertion of an analyte sensor through the skin of a subject.

BACKGROUND

Implantable analyte sensors offer a convenient and accurate alternative to analyte testing methods such as fingerstick blood glucose meters. Indwelling sensors also offer an additional advantage in that analyte concentrations in an individual may be tracked over a period of time without requiring the individual to draw a blood sample for each measurement. Where close attention to blood analyte concentrations is correlated with better outcomes, an indwelling analyte sensor may be superior to other monitoring options. In diabetes, for example, blood glucose levels that are either higher or lower than a target level may result in serious medical complications. Continuously monitoring blood glucose levels using an implanted sensor and an external electronic measuring device may improve the user's ability to control blood glucose levels, thus reducing the incidence and severity of such complications.

Flexible indwelling sensors may be more comfortable for the user than rigid or semi-rigid sensors, and less likely to experience failure due to mechanical stress induced by the user's movements. Flexible indwelling sensors have been described, for example, in U.S. Pat. No. 5,165,407 to Ward et al. However, the insertion of flexible sensors requires an initial piercing of the skin due to the tendency of flexible sensors to bend. Therefore, insertion of flexible sensors is often accomplished by inserting the sensor through a rigid hollow mechanism such as a needle, a cannula or a trocar used to create a channel through which the sensor could pass. See, for example, U.S. Pat. No. 6,695,860 to Ward et al.

The use of such piercing mechanisms for sensor insertion may cause physical and emotional discomfort among users, discouraging the use of indwelling sensors for continuous blood analyte monitoring. Piercing mechanisms that accommodate a sensor may be large and painful to insert through skin. In addition to the physical discomfort associated with piercing mechanisms, an individual in need of consistent blood analyte monitoring may be reluctant to use such a mechanism without assistance.

Analyte sensor flexibility reduces user discomfort in long-term sensor use. But as flexibility increases, the capacity of the sensor to directly penetrate unbroken skin diminishes. While flexible indwelling analyte sensors may improve a user's ability to monitor blood analyte levels for optimal medical outcomes, the available insertion methods may be unacceptable to some who are in need of monitoring.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 5d illustrates a partially exploded perspective view of a SIT in accordance with various embodiments;

DETAILED DESCRIPTION OF DISCLOSED EMBODIMENTS

Figure 1A:
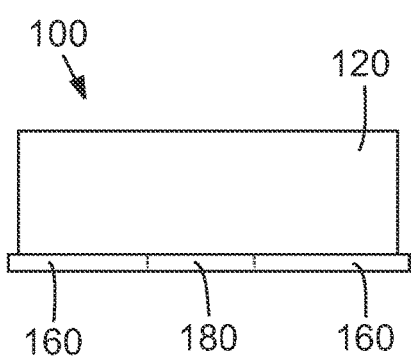
FIGS. 1a-1e show a sensor insertion system and components of a sensor insertion system in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide methods, apparatuses, and systems for inserting a flexible sensor into intact skin. In various embodiments, a sensor insertion tool (SIT) provides the motive force for driving a sensor into intact skin without the use of a needle, trocar, cannula, lancet or similar device to first pierce the skin. In embodiments, a SIT may be reusable and/or disposable, and may be mechanically coupled to one or more other components of a sensor insertion system. In some embodiments, a SIT may be configured to lock securely to one or more components in preparation for sensor insertion. In an embodiment, such a configuration may also include a release element for releasing the SIT and/or a component of a sensor insertion system from another component of the sensor insertion system.

FIG. 1a shows a diagram of a partial sensor insertion system 100 in accordance with various embodiments. Sensor insertion system 100 may include a SIT 120, a channel guide assembly 160, and a sensor subassembly 180. Sensor subassembly 180 may be coupled to channel guide assembly 160. In FIG. 1a, sensor subassembly 180 is retained within an interior aperture of channel guide assembly 160 (shown by dashed lines), but alternatively a sensor subassembly may be positioned at an end and/or edge of a channel guide assembly and/or coupled to a surface by means of a fastener or retaining element. A sensor subassembly 180 may be provided and may be retained prior to insertion within channel guide assembly 160. Channel guide assembly 160 may also be coupled, such as removably coupled, to SIT 120.

In embodiments, a sensor insertion system may be configured to insert a sensor, such as a flexible analyte sensor, into and/or at least partially through a layer of skin and/or into interstitial fluid. A SIT may provide motive force for insertion of a sensor into skin, and a channel guide assembly may provide a channel or track along which the sensor subassembly may travel prior to and/or during insertion of the sensor through the skin. A sensor subassembly may provide electrical communication between the sensor and electrical components in a corresponding part of a sensor assembly. A sensor assembly may comprise one or more components, such as a RSA and DSA.

Embodiments of a sensor insertion system may vary in the number, arrangement, function, and identity of components.

An exemplary embodiment of a sensor insertion system may comprise one or more of a SIT, a channel guide assembly, a sensor subassembly, and a sensor assembly. In operation, a sensor insertion system may be assembled by coupling, such as snapping, locking, etc., together two or more components of a sensor assembly (such as a RSA and a DSA), coupling the sensor assembly to the channel guide assembly, and coupling the SIT to the channel guide assembly. In an embodiment, a channel guide assembly may be provided with a channel guide and a channel guide cover, and may also contain a sensor subassembly pre-positioned for insertion.

The SIT may then be cocked to load energy into a spring member by raising a cocking arm, which may pull a sensor hammer into a pre-insertion position. A trigger element of the SIT may then be actuated, causing release of the sensor hammer and the loaded energy; this may cause the hammer to strike the sensor subassembly positioned within the channel guide, driving the sensor subassembly down a channel of the channel guide with sufficient force to drive the sensor through a channel in the sensor assembly and into/through intact skin without the use of a trocar or other such element. The provided force may also be sufficient to drive a housing of the sensor subassembly into a recess of the sensor assembly, causing sensor contact elements of the sensor subassembly to contact corresponding contact elements within the sensor assembly. This contact may provide an electrical connection from the sensor to the circuitry of the sensor assembly. Finally, a release member of the SIT may be actuated to apply force against retention elements of various components, uncoupling the SIT and/or channel guide from the sensor assembly and sensor subassembly. The sensor assembly and sensor subassembly may remain affixed to the skin, such as by an adhesive or adhesive patch, after the uncoupling of the SIT and/or channel guide.

Figure 1B:
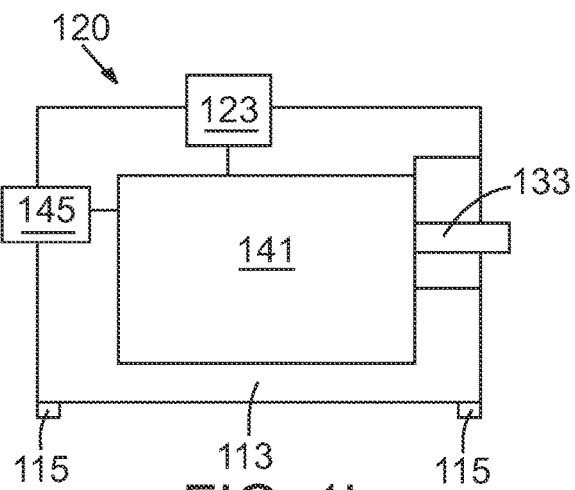

FIG. 1b shows a diagram of a SIT 120 in accordance with various embodiments. SIT 120 may include a cocking member 133, an actuator 123, a release member 145, a motive force member 141, a housing 113 and/or a locking element 115. In FIG. 1b, cocking member 133, actuator 123, and release member 145 are coupled to motive force member 141, and housing 113 is coupled to locking element 115 and to each of the other components. Alternatively, a housing may be mechanically coupled to a component of a sensor insertion system, such as a channel guide assembly, and may not be coupled to the other components of the SIT.

A cocking member may be configured to permit cocking a SIT only when sensor insertion components are in a correct position for sensor insertion. Some embodiments may comprise a cocking member release that releases energy loaded without causing sensor insertion.

In a sensor insertion system, a SIT may be configured to apply motive force to a sensor and/or to a sensor subassembly coupled to and/or or retained within a channel guide or other component. The applied force may propel the sensor through an aperture or channel within a channel guide or other component such that the sensor is driven through the aperture/channel and into skin without the use of means for piercing the skin prior to insertion.

Motive force may be generated by one, two, three, four, or more springs. A cocking member may be used to load and store energy in one or more springs. The release of such stored energy may drive a sensor and/or sensor assembly toward the skin for sensor insertion. A cocking member may only require a single manipulation by a user to store sufficient energy for sensor insertion, while in other embodiments, a cocking member may be manipulated two or more times to store energy for insertion. A cocking member may be configured to minimize the force required to load sufficient energy in the spring for sensor insertion, allowing the user to apply minimal force to the cocking member. A cocking member may be configured to be moved up, down, to the side, pushed inward, and/or pulled outward to load energy into the spring.

In some embodiments, a spring member may be associated with a ratchet or similar element, and a user may load energy into the spring member for sensor insertion by repeatedly pushing, pulling, sliding, raising, or otherwise manipulating the ratchet. In an embodiment, a trigger element may adjust the position of the ratchet or other associated component to release the loaded energy from the spring.

While springs are discussed above as providing motive force, any suitable device may be utilized to provide the desired motive force. For example, motive force may be provided by a chemical reaction and/or by compression/expansion of a gas or other substance, electromagnetically, mechanically, or by other means, individually or in combination. A SIT may include a chamber for gas compression, a piston fitted within the chamber, and a one-way flow valve that allows air to enter but not to escape. For example, a cocking member may be used to prime a mechanism providing motive force from a chemical reaction and/or expansion/compression of a gas. A user may manipulate a handle or lever element attached to the piston, compressing air within the chamber. In an embodiment, the release of compressed air may be applied against a sensor subassembly with sufficient force to drive a sensor into and/or through skin. In other embodiments, a compressed gas such as carbon dioxide may be supplied in a single-use canister and coupled to a SIT to provide motive force for sensor insertion.

One or more components of a SIT may comprise a shape memory material, such as a shape memory alloy, a shape memory polymer and/or another thermally-responsive material. In some embodiments, a component of a SIT that provides motive force may respond to a change in temperature by changing its conformation. For example, a spring force member may be configured to assume a first state in response to application of heat to the spring force member, and to assume a second state in response to cooling of the spring force member. In embodiments, heating/cooling a SIT component may provide motive force for sensor insertion. Alternatively, heating/cooling a SIT component may cause a change in configuration of the component such that another component is moved, triggered, locked, released, or retained.

A shape memory alloy may contain copper, zinc, aluminum, nickel, and/or titanium, or any combination of these. Shape memory polymers may contain polyurethanes and/or block copolymers, and a SIT component comprising a shape memory polymer may change its shape/conformation in response to one or more of heat, light, electricity, change in pH, and/or a magnetic field. In some embodiments, a plurality of components of a SIT may comprise a shape memory material. A SIT may be configured to be reusable; in some embodiments, the application of heat/light/electricity/magnetic field to the SIT and/or exposure of the SIT to a pH change may return a SIT to its original conformation after a use of the SIT.

In embodiments, a sensor assembly may be adapted to adhere to the skin and/or to apply force to skin near the insertion site to stretch or pull the skin prior to sensor insertion. In an embodiment, a channel guide assembly may be provided with a suction means to pull skin toward the channel guide assembly. Alternatively, a suction means may be provided by actuating a SIT or may be activated separately using a button, a plunger, a cocking mechanism, and/or another user control element.

Figure 1C:
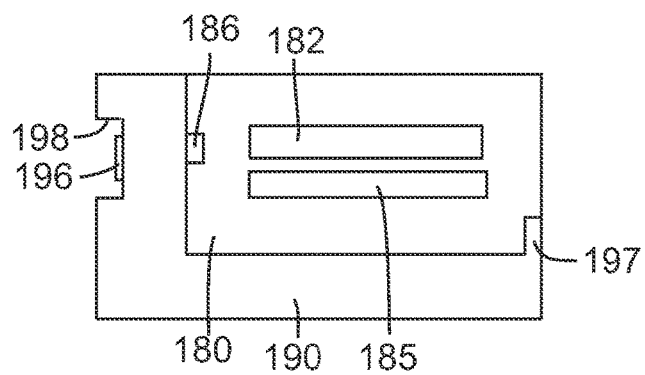

FIG. 1c illustrates a diagram of a sensor assembly in accordance with various embodiments. FIG. 1c includes a first sensor assembly component 180, a second sensor assembly component 190. First sensor assembly component 180 may include a battery 185, electronic circuitry 182, and/or electrical contacts 186. Second sensor assembly component 190 may further include a retention element 197 for coupling components 180,190 and/or a retention clip 196 for securing a sensor subassembly (not shown) in recess 198. The first and the second sensor assembly components may be configured to be mechanically coupled together, and may be further configured to be releasable from one another. While FIG. 1c illustrates a sensor assembly with two main components, a sensor assembly may instead be provided with one, two, three or more components.

In embodiments, a sensor assembly may provide electrical communication with a sensor that has been inserted into skin. A component of a sensor assembly (such as the first or the second component) may comprise one or more housing elements, electronic circuitry (e.g. one or more printed circuit boards), electrical contacts, power sources, gaskets and/or sealants, and/or one or more means for being mechanically coupled to another component of a sensor insertion system. Such means may include a clip, a surface feature and/or protrusion of a housing element or other element of the component, a screw member, a pin member, a hinge member, a lip or thread, a slot, a pivot, etc.

A power source may include a single battery or two or more batteries connected in parallel and/or in series, and may comprise an electrochemical battery, a disposable battery, and/or a rechargeable battery. Power may be provided by the motion of the user. A component of a sensor assembly and/or a sensor insertion system may be provided with means to convey battery life and/or power level via a visual, audio, and/or tactile signal.

Components of a sensor assembly may vary as desired for particular applications. In embodiments, one, two or more of the components of a sensor assembly may be disposable and/or reusable.

Figure 1D:
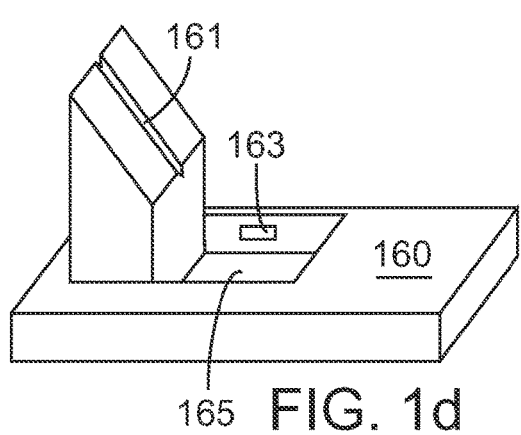

FIG. 1d illustrates an embodiment of a channel guide 160. Channel guide 160 comprises a channel 161, a retention element 163, and an aperture 165. Other embodiments may lack one or more of these features and/or may include additional features. While not shown, channel guide 160 may be configured to couple to a channel guide cover and at least partially enclose channel 161, or such a cover may be an integrated component of channel guide 160.

A channel guide may provide a channel, groove, aperture, and/or other such feature to accommodate a sensor and/or a sensor subassembly. A channel guide cover may be coupled to a channel guide to create a path for a sensor and/or sensor subassembly. A channel guide may have any suitable shape and thickness, and may be either disposable or reusable. In embodiments, a channel guide may be configured with one or more retention elements for mechanically coupling the channel guide to a sensor assembly, a sensor assembly component, a SIT, a channel guide cover, and/or any combination thereof. Such retention elements may include slots, protrusions, fasteners, adhesives, etc. Retention elements may be configured to reversibly mechanically couple the channel guide and another component of a sensor insertion system.

A channel guide may include one or more apertures, depressions, raised features, etc. to accommodate one or more components such as a sensor assembly and/or its component(s), a SIT, and/or a sensor subassembly. A channel guide may include a raised surface protrusion that defines a path for a sensor and/or sensor subassembly.

Figure 1E:
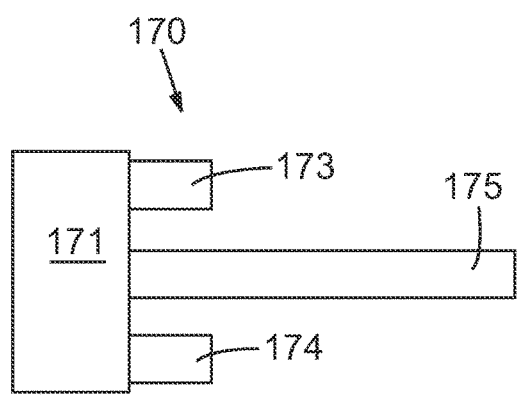

FIG. 1e illustrates a sensor subassembly 170 in accordance with embodiments. A sensor subassembly 170 includes a housing 171, a sensor contact 173, a sensor contact 174, and a sensor 175. One, two, three, four or more sensor contacts may be coupled to a sensor. A housing may partially enclose some or all of these components. A housing may be provided with one or more surface protrusions or other features configured to mate with one or more features of a channel guide and/or another component of a sensor insertion system.

Details regarding embodiments of sensor subassemblies may be found described in the figures and text of U.S. Patent Application No. 61/037,246, filed Mar. 17, 2008, entitled "Analyte Sensor Subassembly and Methods and Apparatuses for Inserting an Analyte Sensor Associated with Same," the entire disclosure of which is incorporated by reference in its entirety.

In an embodiment, a sensor insertion system may lack a channel guide. If lacking a channel guide, a sensor may be held in position by a component of a SIT and/or by another component.

A sensor insertion system may lack an adhesive member, and thus a sensor assembly may be held to the skin with a separate element such as a band, a belt, a separately applied adhesive such as a dissolvable tissue adhesive, a bandage, a garment, or other means. An adhesive member may be adapted for placement over the top surface of a sensor assembly.

A sensor insertion system may be provided with features to assist end users with physical impairments in the use of such systems. In embodiments, a SIT, a channel guide, a housing, and/or other component(s) may be configured with raised surface details to aid a visually impaired end user in the assembly and/or use of sensor insertion systems. A housing at least partially enclosing one or more components may be ergonomically designed to be held and/or used for sensor insertion with one hand, and/or the surface of the housing may comprise surface detail and/or a material to improve the user's ability to grip the housing (e.g. rubber, plastic, an elastomer, etc.).

In an embodiment, a SIT or other component of a sensor insertion system may further comprise a visual, tactile and/or auditory signal conveying that a sensor has been inserted, that a sensor has not been inserted, that a malfunction has occurred, and/or that a period of time has passed (e.g. due for insertion of new sensor, shelf life of component has expired, etc.). Actuation of one or more components may trigger an auditory signal to convey that actuation was or was not completed. Some embodiments may further include a light source to illuminate skin and/or a component of the sensor insertion system.

A sensor insertion system may be provided with a feature that prevents actuation of the SIT if two components are misaligned or not mechanically locked into position.

Various components of a sensor insertion system may be configured for assembly by an end user prior to sensor insertion. A SIT may be packaged and/or supplied to an end user separately from other components of a sensor insertion system, while in other embodiments a SIT may be provided in combination with a channel guide assembly, one or more components of a sensor assembly, an adhesive member, and/or a sensor subassembly. Some or all of the components of a sensor insertion system may be configured to be mechanically coupled such that they are locked into an optimal position for sensor insertion. In embodiments, the locking of one or more components may be reversed by actuating a release mechanism.

A channel guide assembly may be provided coupled to a DSA and containing a sensor subassembly. Such a channel guide assembly may then be coupled to a SIT for sensor insertion. A RSA may be coupled to the DSA either before or after coupling the channel guide assembly and the SIT. A RSA may be coupled to the DSA either before or after sensor insertion.

A SIT and a channel guide assembly may be provided as a single unit, with one or more components of a sensor assembly being coupled to the unit by insertion of the component(s) into the unit through an opening in the single unit, such as a slot and/or pocket in the top, bottom or side of the single unit. A SIT and a channel guide assembly may be provided as a single unit with a sensor assembly and/or a sensor subassembly pre-positioned within or coupled thereto. A SIT and channel guide assembly may be provided as a single unit with a sensor pre-positioned within, requiring only the placement of a sensor assembly by the user or by another into the single unit.

In an embodiment, a SIT and channel guide assembly may be provided as a single unit which includes a disposable portion of a sensor assembly, requiring only the placement of a reusable portion of the sensor assembly into the single unit by the user or by another. A SIT and channel guide may be provided as a hinged unit configured to be opened for placement of one or more components (such as a sensor assembly or a sensor subassembly).

A SIT and/or a channel guide assembly may be provided as one, two, three, four, five or more components to be assembled by the end user. Some embodiments of a sensor insertion system may include a detachable housing to enclose part or all of one or more components.

Figure 2A:
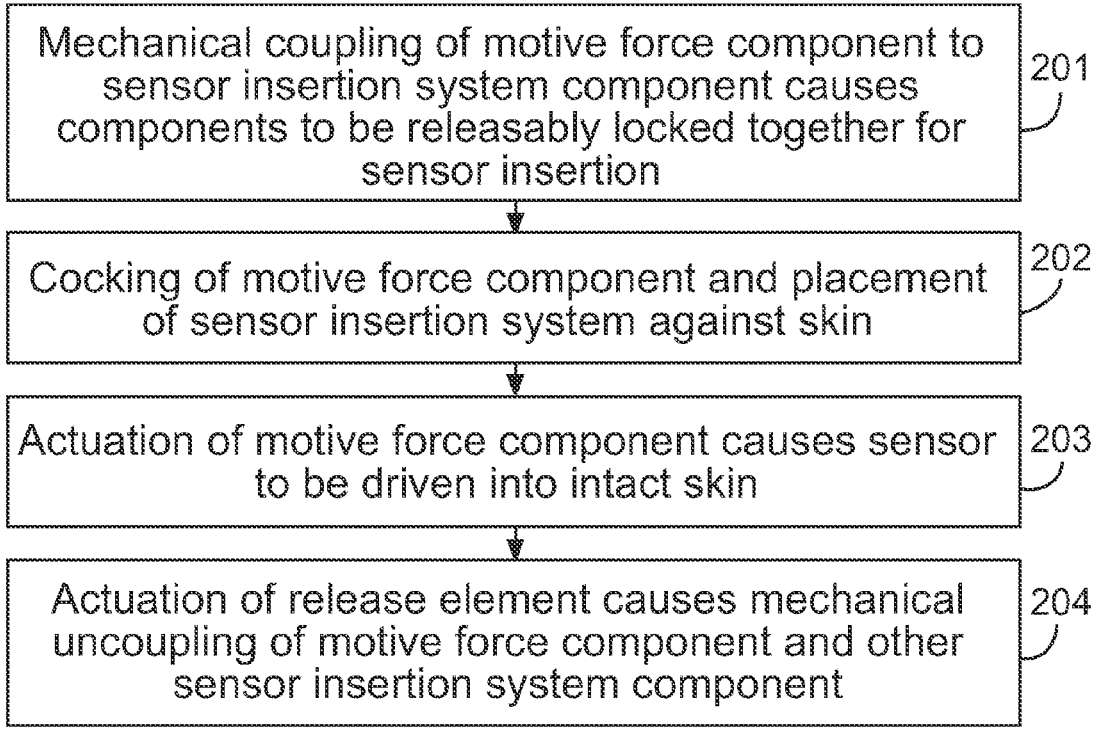
FIGS. 2a and 2b show flow charts for methods of sensor insertion using a sensor insertion system in accordance with various embodiments.
Figure 2B:
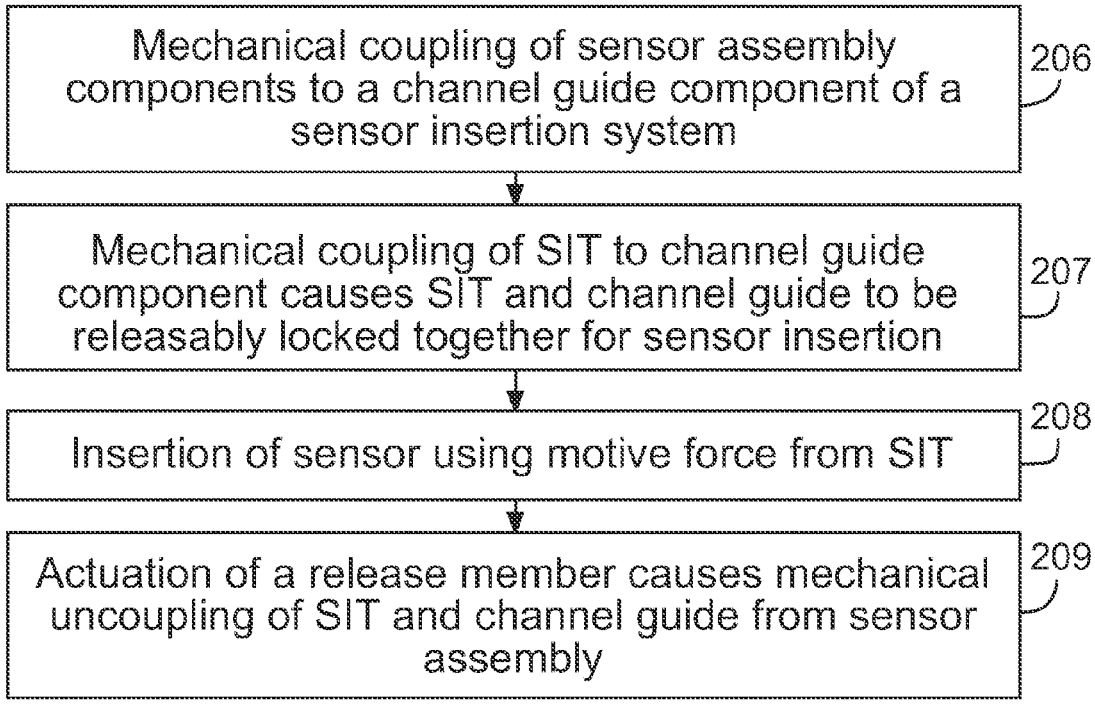

FIGS. 2a and 2b show flow charts for methods of using a sensor insertion system. FIG. 2a shows a flow chart for a method of using a sensor insertion system comprising a motive force component (e.g. a SIT) that is coupled to other components prior to sensor insertion. First, at step 201, the motive force component is mechanically coupled to another component of a sensor insertion system, such as a channel guide assembly, a sensor assembly, or other component, releasably locking together the motive force component and other component(s). Next, at step 202, the motive force component is cocked and the sensor insertion system is placed against skin. A motive force component may be configured for cocking before and/or after placement of a sensor insertion device against skin. At step 203, the motive force is actuated, causing the sensor to be driven into the skin. Actuation of the motive force may occur through physical manipulation of a trigger or actuator coupled to the motive force component. Actuation of the motive force may occur in response to manipulation of a user interface element of a sensor insertion tool, such as a button, a key, a touchpad, a dial or wheel, etc. At step 204, actuation of a release element causes the motive force component to become mechanically uncoupled from other sensor insertion system components such as a sensor assembly. Actuation of a release element may release both a motive force component and a channel guide assembly or other component from a sensor assembly. In an embodiment, a release button is not provided and unlocking/dissociation of the motive force component occurs as a result of sensor insertion. For example, a portion of the motive force for sensor insertion may be used after insertion to release/unlock the motive force component from another component.

FIG. 2b shows a flow chart for a method of sensor insertion using a sensor insertion system that provides sensor assembly components as separate components to be assembled by an end user, a physician, a caretaker, etc. In step 206, one or more sensor assembly components are mechanically coupled to a channel guide component of a sensor insertion system. In step 207, the channel guide/sensor assembly is mechanically coupled to a SIT and the coupling causes the SIT and channel guide component to become locked together in position for sensor insertion. In step 208, the sensor is inserted with motive force provided by the SIT. Last, in step 209, actuation of a release member causes the SIT and channel guide to uncouple/unlock from the sensor assembly. In some embodiments, the SIT and channel guide may also dissociate from one another, while in other embodiments they remain mechanically coupled after actuation of the release member. In some embodiments, the SIT and channel guide may be re-used, while in other embodiments one or both are disposable and/or configured for a single use.

Figure 3:
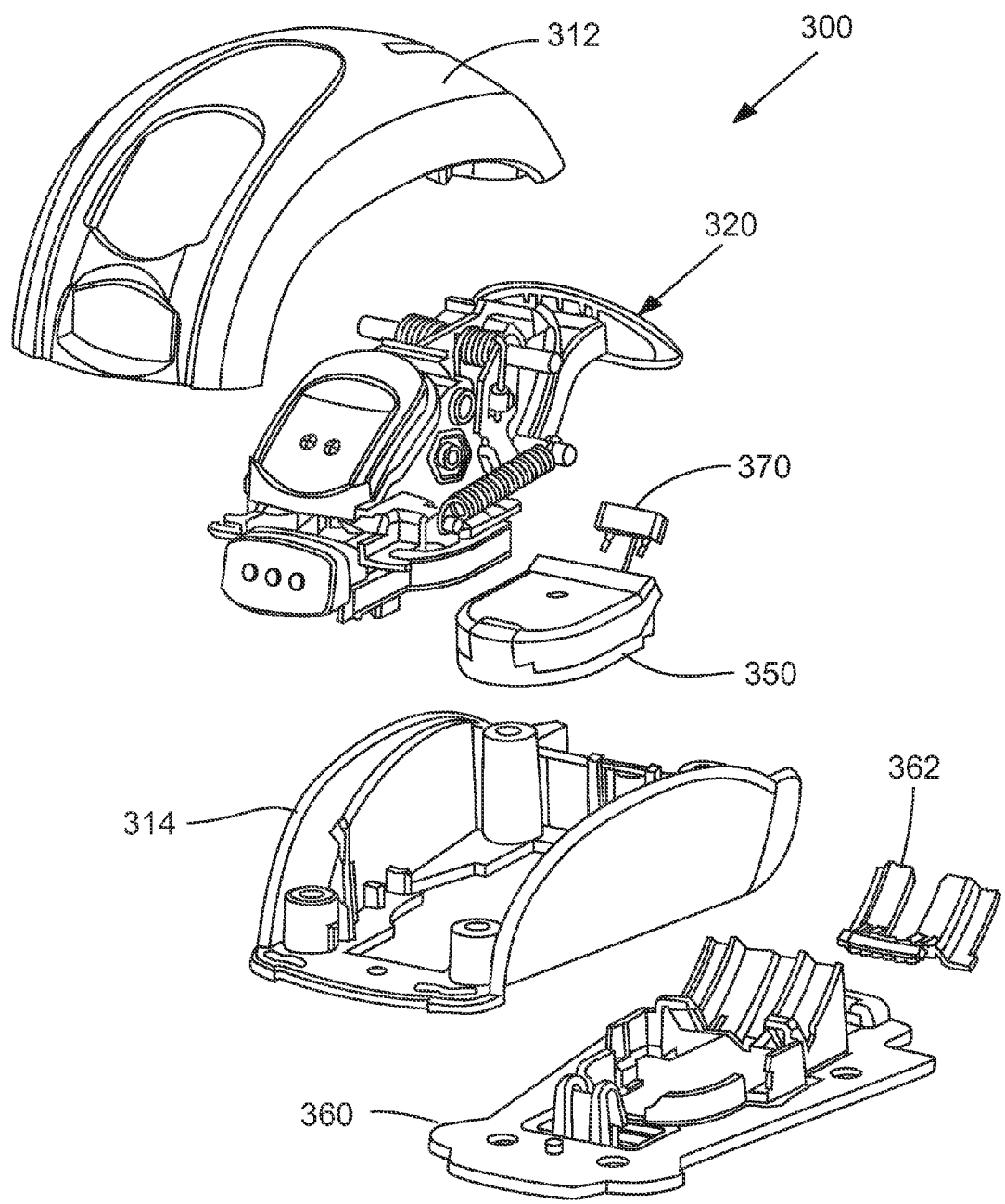
FIG. 3 shows a partially exploded perspective view of a sensor insertion system for insertion of a sensor into intact skin in accordance with various embodiments.

FIG. 3 shows a partially exploded perspective view of a sensor insertion system 300. Sensor insertion system 300 may include SIT top housing element 312, SIT bottom housing element 314, SIT mechanics 320, channel guide 360, channel guide cover 362, sensor assembly 350 and/or sensor subassembly 370. Housing element 312 may be coupled to mechanics 320 and to housing element 314. Channel guide 360 may be coupled to sensor assembly 350 and to channel guide cover 362. One or more components of sensor subassembly 370 may be configured to be retained within an opening defined by channel guide cover 362 and channel guide 360 prior to sensor insertion.

A top housing element may have one or more apertures to accommodate certain features of the SIT (e.g. a release member, a trigger button, a cocking handle), allowing the features to be accessible to a user. A housing element may also include one or more apertures for indicating the status of the SIT (e.g. cocked or uncocked, positioned or not positioned for sensor insertion, etc.) and/or for accommodating a light, a speaker, or other feature. A top housing element may be reversibly or permanently coupled to a bottom and/or other housing element with one or more screw members or pins, an adhesive, a hinge, a snap, a rivet, a clip, or other fastener(s). Alternatively, a housing element may comprise one or more integrated protrusions, slots, and/or other features configured to allow mechanical coupling of the housing element and another component without additional fasteners.

A bottom housing element and/or a top housing element may have surface features configured to accommodate one or more parts of a sensor assembly or channel guide assembly and/or one or more members for mechanical coupling of components. A bottom housing element may include an aperture configured to accommodate the coupling of a channel guide assembly to the bottom housing element, and/or an aperture to accommodate one or more other components of a sensor assembly.

While FIG. 3 shows two housing elements, embodiments may have one, two, three, or more housing elements. A housing element may be constructed from plastic, resin, a polymer, or any other suitable material. A housing element may be constructed of a lightweight, inexpensive, durable, and rigid/semi-rigid material. The color/opacity/translucence of a housing element may vary as desired, and may vary even among different parts of a single housing element—for example, some embodiments may include a housing element that is clear in one area for improved viewing of the SIT mechanics and opaque or semi-opaque in another area.

Figure 4:
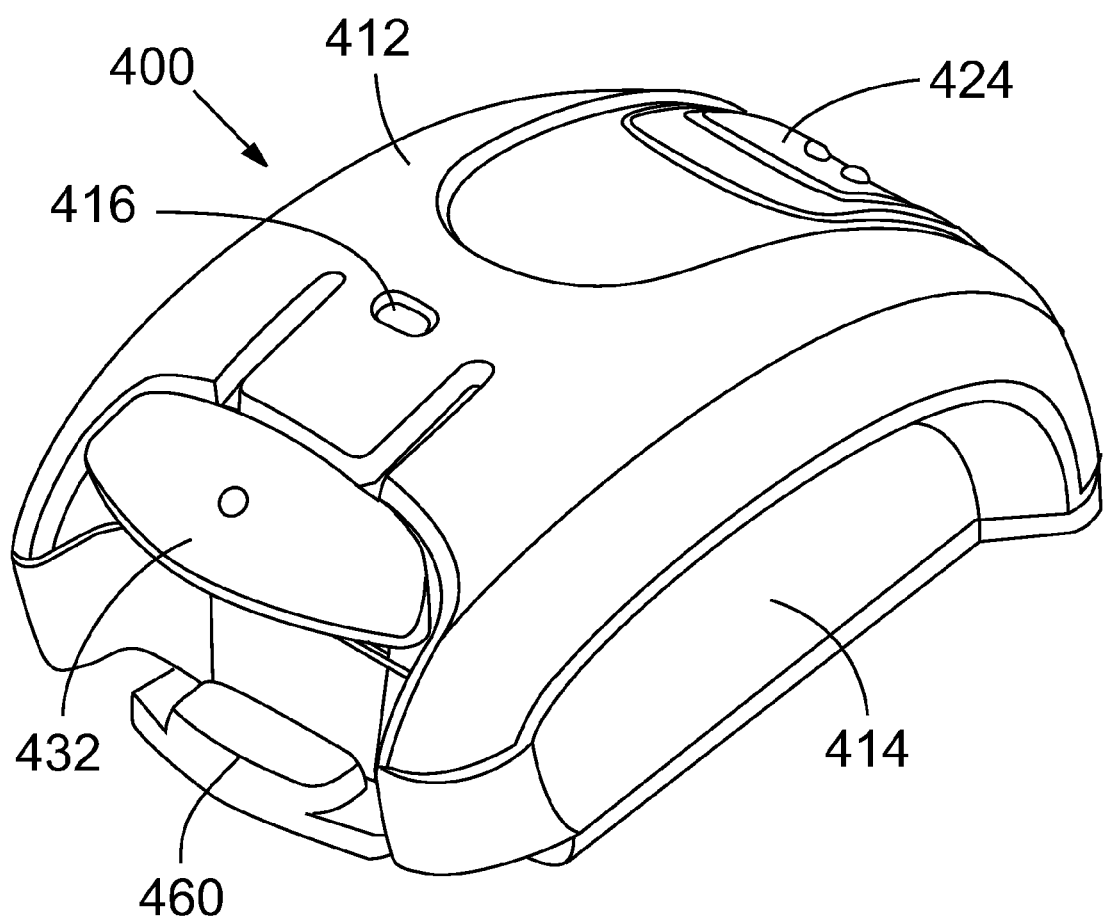
FIG. 4 shows a perspective view of a sensor insertion system in accordance with various embodiments.

FIG. 4 shows a perspective view of a sensor insertion system 400. System 400 includes a top housing 412, a bottom housing 414, a cocking indicator window 416, a trigger button 424, a cocking handle 432, and a channel guide 460. Top and bottom housing may be mechanically coupled and may enclose at least some portion of the SIT components. Channel guide 460 may be mechanically coupled to housing 414 and/or to the SIT components. Top housing 412 may have one or more apertures and/or surface features to accommodate cocking indicator window 416, trigger button 424, and cocking handle 432. A cocking indicator, such as a cocking indicator window, is configured to convey to a user that the motive force component is or is not cocked. Alternatively, cocking may be indicated by an auditory, vibratory/tactile, or other visual signal (e.g. a light, a color change, protrusion of a feature, etc.). Alignment, or lack thereof, of one or more components may be signaled by any of these means alone or in combination.

Figure 5A:
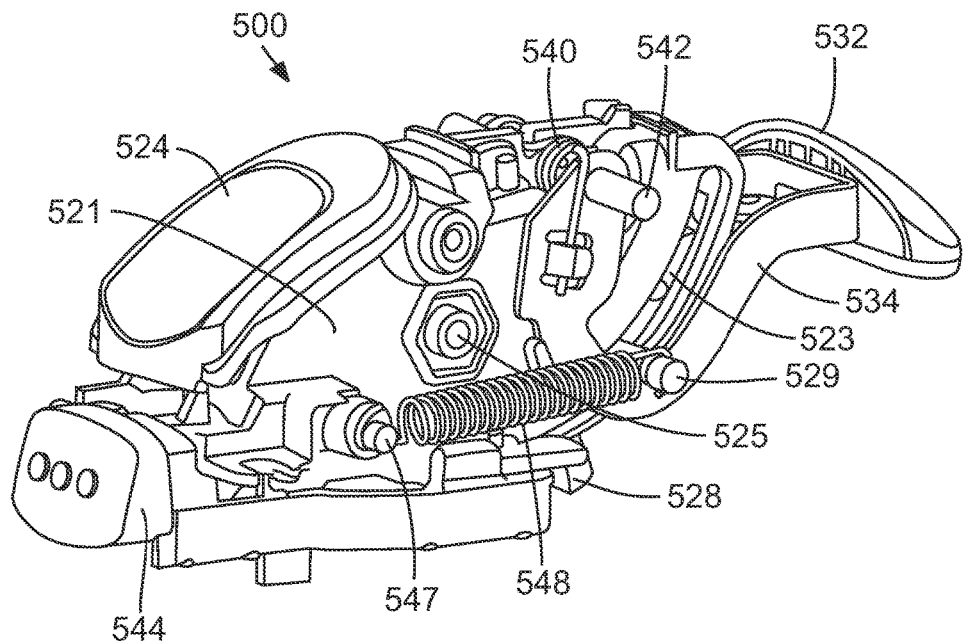
FIG. 5a illustrates a perspective view of the interior of a sensor insertion tool (SIT) configured to provide a motive force for sensor insertion in accordance with various embodiments.
Figure 5B:
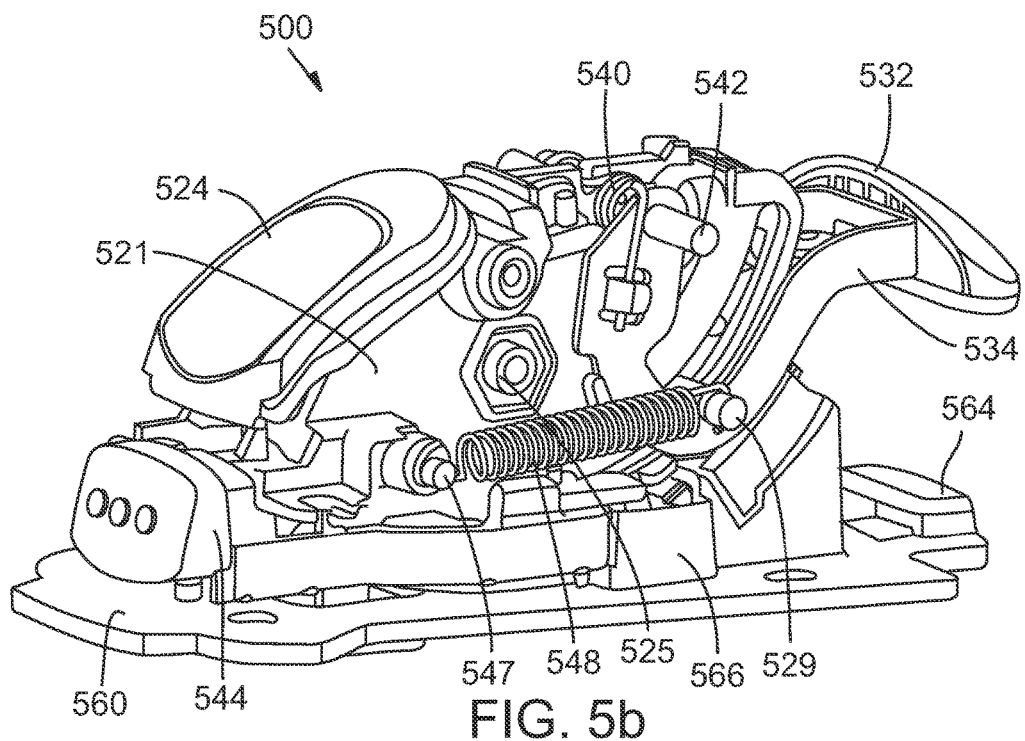
FIG. 5b illustrates a perspective view of the interior of a SIT coupled to a channel guide assembly in accordance with various embodiments.
Figure 5C:
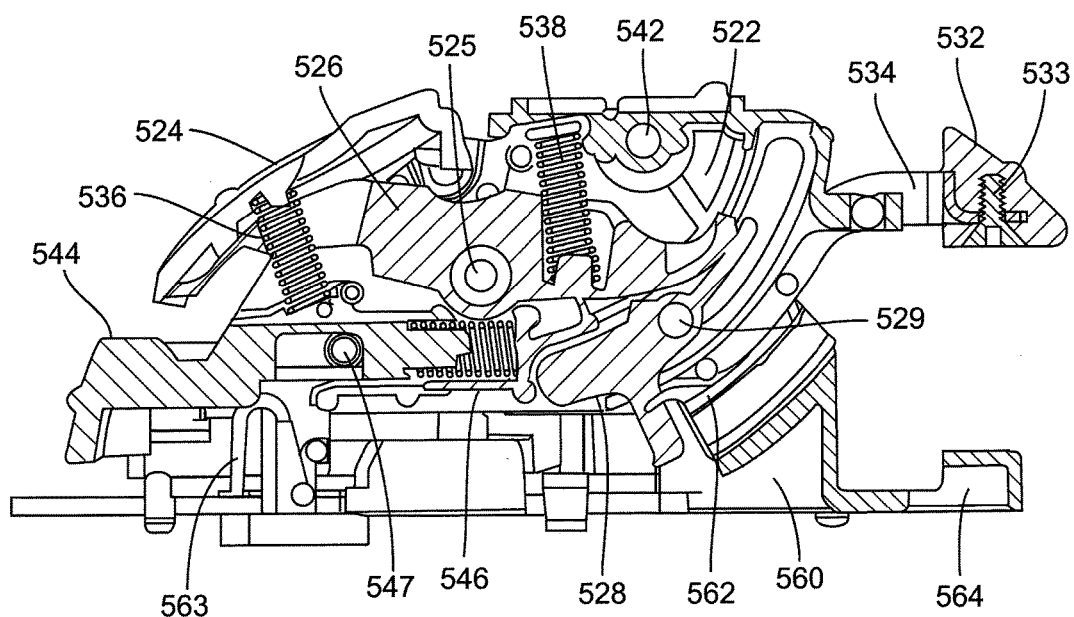
FIG. 5c illustrates a cutaway view of a SIT mated to a channel guide assembly in accordance with various embodiments.

FIG. 5a illustrates a perspective view of the interior mechanics of a sensor insertion tool (SIT) 500 (with the housing removed) configured to provide a motive force for sensor insertion. In FIG. 5b, SIT 500 is shown mechanically coupled to a channel guide assembly 560. FIG. 5c illustrates a cutaway view of SIT 500 mechanically coupled to a channel guide assembly 560. FIG. 5d illustrates a partially exploded perspective view of SIT 500.

The embodiment illustrated in FIGS. 5a-5d comprises a left frame 521 and a right frame 522, a cocking handle 532, a cocking handle screw 533, a cocking arm 534, a double torsion spring 540, a double torsion spring pin 542, a release member 544, a release member compression spring 546, a trigger button 524, a trigger pivot 525, a trigger arm 526, a front trigger compression spring 536, a rear trigger compression spring 538, a left extension spring 548, a right extension spring (not shown), an extension spring pin 547, a hammer pin 529, and a hammer 528. FIGS. 5b and 5c also include a channel guide assembly 560 with retention element 563 and retention slot 564. Additionally, left frame 521 and right frame 522 include a hammer channel 523.

Left frame 521 and right frame 522 are mechanically coupled such that hammer channel 523 accommodates hammer pin 529, which is positioned horizontally through hammer channel 523 such that one end of hammer pin 529 protrudes through each frame 521, 522. Trigger pivot 525, extension spring pin 547, and double torsion spring pin 542 are likewise horizontally positioned to protrude through both frame members. Double torsion spring 540 is mechanically coupled to a cocking mechanism comprising cocking arm 534, cocking handle 532, and cocking handle screw member 533. Double torsion spring 540 also encircles double torsion spring pin 542 and passes through a notch/channel of the coupled frames 521, 522.

Trigger button 524 is mechanically coupled to left frame 521 and right frame 522 by a surface feature and/or fastener. Trigger button 524 is mechanically coupled to front trigger compression spring 536, which passes through a vertical aperture in trigger arm 526 and is accommodated by a surface of left frame 521 and right frame 522. Front trigger compression spring 536 applies upward pressure on trigger button 524, increasing the amount of force that the user must apply to trigger button 524 to release the hammer, and improving the ergonomic feel of trigger button 524. Rear trigger compression spring 538 is in mechanical contact at one end to an interior surface of a top housing (not shown) and in mechanical contact to an indented surface of trigger arm 526 at the other end, applying a downward force to the rear of trigger arm 526. Trigger arm 526 pivots a limited distance around trigger pivot 525.

Release button 544 is positioned below trigger arm 526 and is coupled to left frame 521 and right frame 522 by extension spring pin 547, which passes horizontally through an aperture in release button 544 and also through left frame 521 and right frame 522. Extension spring pin 547 is coupled at its right end to the right extension spring (not shown, but symmetrical to spring 548) and at its left end to left extension spring 548. Hammer pin 529 is coupled in the same manner to the other ends of the right extension spring and left extension spring 548.

In operation, the SIT may be coupled to a channel guide assembly. Pressure is applied to cocking handle 532 in an upward direction by a user to cock the SIT for sensor insertion. Pulling upward on cocking handle 532 forces hammer pin 529 and hammer 528 upward along hammer channel 523, and pulls left extension spring 548 and the right extension spring backward and upward, loading energy in the extension springs. With cocking handle 532 in an upright position, trigger arm 526 tilts around trigger pivot 525 due to downward force applied to the rear of trigger arm 526 by rear trigger compression spring 538 (which pushes the rear of trigger arm 526 downward). As cocking handle 532 is released, the newly positioned trigger arm 526 stops the hammer 528 from returning to its initial position at the bottom of hammer channel 523, cradling the bottom of hammer 528 within a surface feature configured to mate with hammer 528.

Hammer 528 may then be released by pressing trigger button 524, which forces the trigger arm 526 to pivot such that the rear of trigger arm moves upward until it no longer accommodates hammer 528 within hammer channel 523, releasing hammer 528 to be forced rapidly along hammer channel 523 by the energy loaded in the extension springs.

After sensor insertion, the SIT and the channel guide 560 may be uncoupled/unlocked from the sensor assembly by applying pressure to release member 544. Release member 544 is pushed toward the back of the SIT, pushing retention member 566 outward such that vertical retention members adapted to retain a sensor assembly are pushed away from the sensor assembly. This causes the SIT and the channel guide to be unlocked and/or disengaged as a unit from the sensor assembly, which remains on the skin. The SIT may then be disengaged from the channel guide 560 by manually pushing retention element 563 with one or more fingers. In the illustrated embodiment, retention element 563 may be pushed to the left (as represented in the figure) in order to disengage the SIT from the channel guide 560, but in other embodiments a retention element may be pushed in one or more other directions, such as forward, backward, up, or down in order to disengage the SIT from the channel guide 560.

A SIT may be securely coupled and/or reversibly locked to a channel guide through one or more retention elements/features, such as retention element 563, retention member 566, and/or retention slot 564. In some embodiments a SIT may be securely coupled and/or locked (either reversibly or irreversibly) to a channel guide through one or more snaps, screws, pins, or other mechanical fasteners. A SIT may be pressed against a channel guide such that a retention feature of the SIT and/or channel guide locks the SIT and channel guide into position for sensor insertion. A channel guide may be pressed against a sensor assembly for locking in the same or similar manner. A retention element may be used for locking components together, for separating components after sensor insertion, or both. For example, a retention element may be configured to be mechanically coupled to a component of a SIT (e.g. the frame, a release button, a pivot, a trigger arm, etc.) and may be uncoupled from the SIT by actuation of a release button and/or by manipulation of the retention element itself. In an embodiment, a retention member (e.g. retention member 566 shown in FIG. 5b) may operate to securely couple a sensor assembly to a channel guide, and actuation and/or force applied to a release member (e.g. release button 544 shown in FIG. 5b) may force the release member against the retention member, pushing the retention member away from the sensor assembly and uncoupling the sensor assembly from the channel guide. In some embodiments a release mechanism may comprise two or more retention members and/or release elements that interact to release a sensor assembly from a channel guide. In embodiments, pressing a release button may push a first release/retention element backward to contact a second release/retention element, and the second release/retention element may then push against a sensor assembly, separating the sensor assembly from the channel guide (see e.g. FIG. 9f, described below).

The number and configuration of SIT components may vary among embodiments. For example, a SIT may comprise a single frame member, while other embodiments may include electronic circuitry and/or additional features. One or more spring members may be replaced with another source of motive force such as a carbon dioxide cartridge.

A SIT may be individually packaged/provided. In other embodiments, a SIT may be packaged/provided with additional components of a sensor insertion system.

Figure 6A:
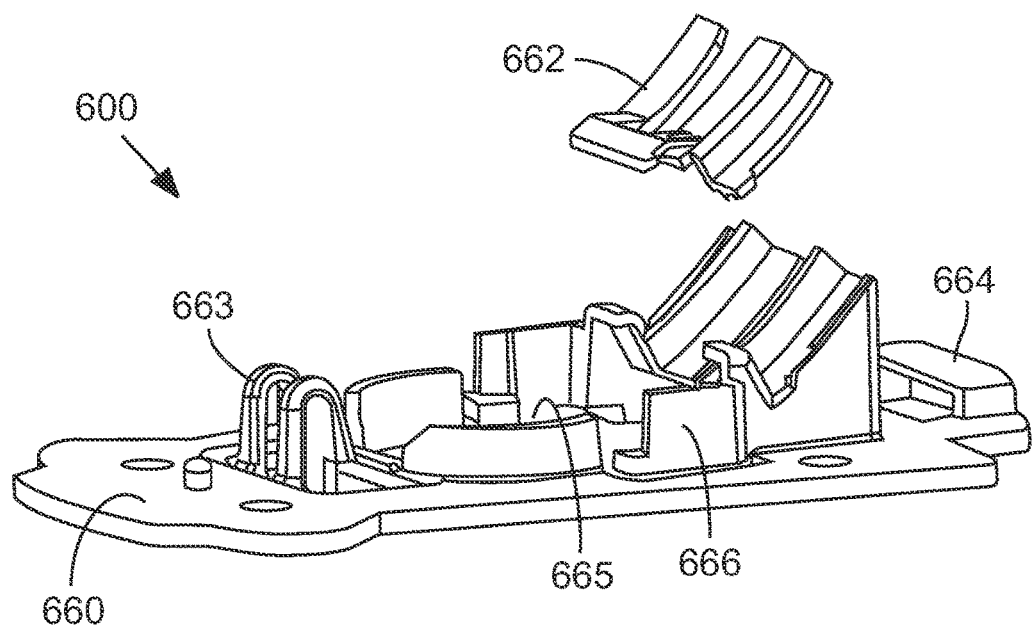
FIGS. 6a-6d illustrate a channel guide assembly comprising a channel guide and a channel guide cover in accordance with various embodiments.
Figure 6B:
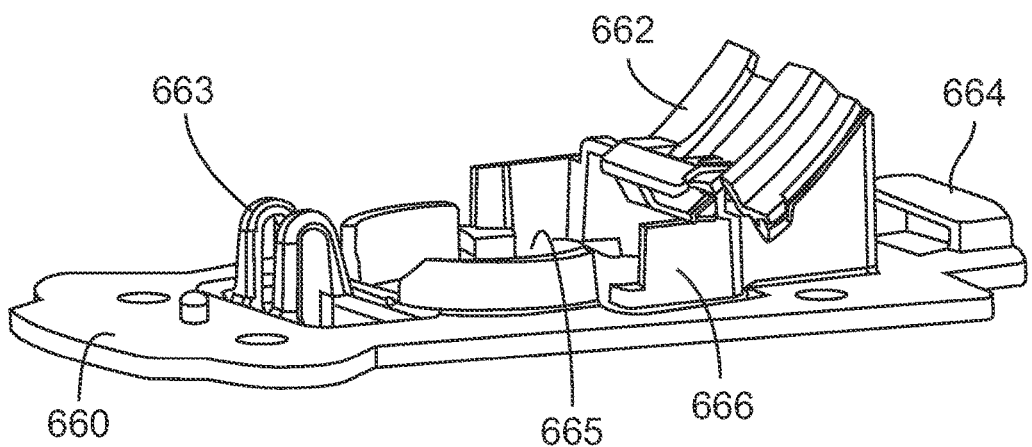
Figure 6C:
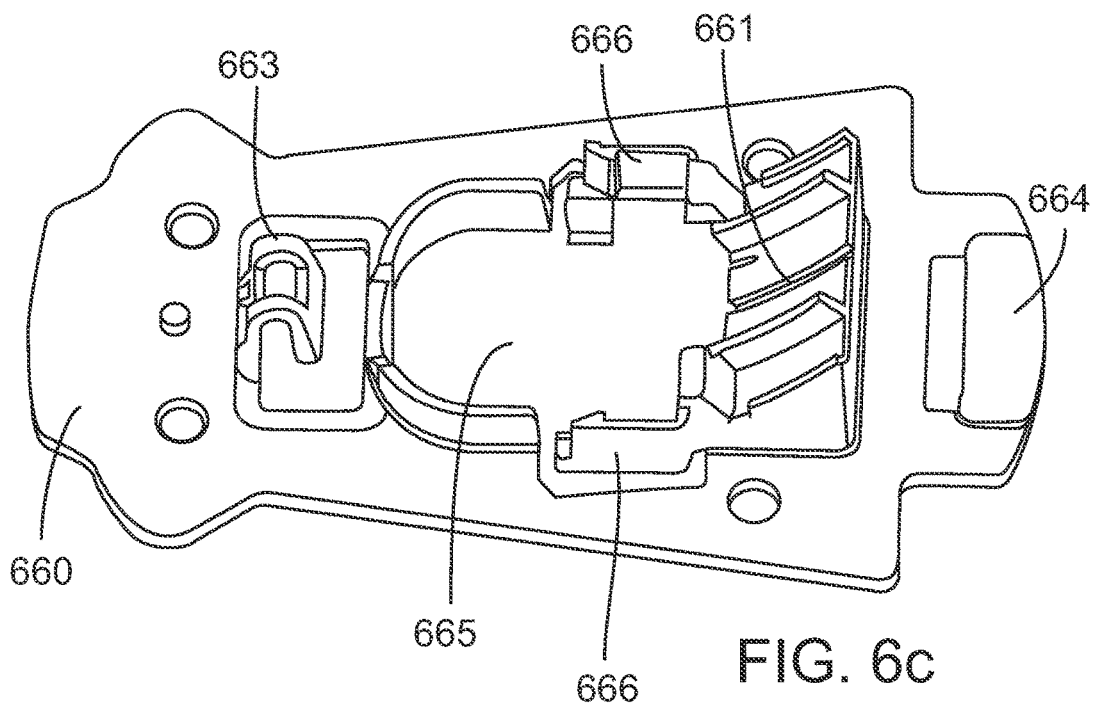
Figure 6D:
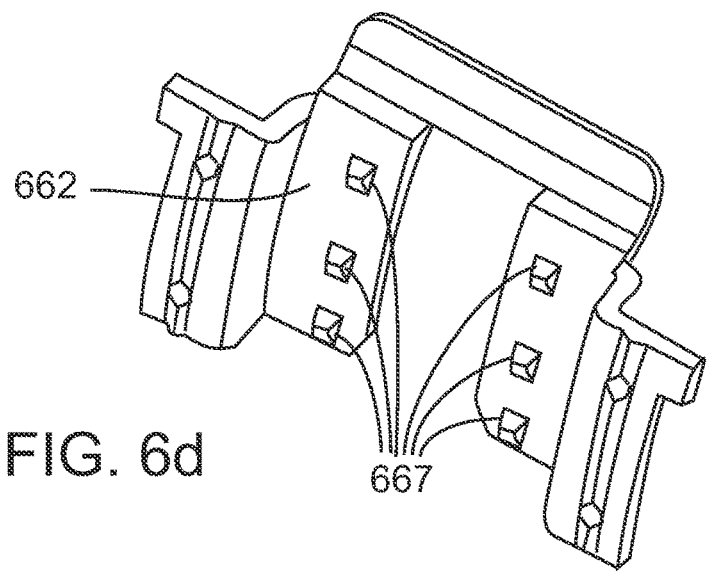

FIGS. 6a-6d illustrate a channel guide assembly 600 comprising a channel guide 660 and a channel guide cover 662 in accordance with various embodiments. FIG. 6a is a partially exploded view of a channel guide assembly 600. FIG. 6b shows the channel guide 660 and channel guide cover 662 in position for sensor insertion. FIG. 6c shows surface features of a channel guide assembly 600. FIG. 6d shows surface details of a channel guide cover 662.

A channel guide assembly 600 may have an aperture 665, a retention element 663, retention members 666, a channel 661, a retention slot 664, and/or a channel guide cover 662. Channel guide cover 662 may comprise protrusions 667 on one or more surfaces to assist in retention and alignment of an associated sensor subassembly (not shown). Channel guide 660 may be configured for integration with a SIT, a sensor assembly, a sensor subassembly, or with any combination of these. In an embodiment, a channel guide assembly 600 may be disposable and may be discarded after a single use.

A channel guide and channel guide cover may be provided separately, together, or as a single unit in which the channel guide cover is not removable from the channel guide. A channel guide and channel guide cover may be provided with a sensor subassembly pre-positioned within for insertion. A channel guide may be provided with a sensor assembly and/or a SIT, either separately/uncoupled or as a coupled unit.

A channel guide cover may include one or more protrusions or pairs of protrusions configured to retain a sensor subassembly in a position for insertion until a motive force is applied to the sensor subassembly. Protrusions may also or alternatively improve or maintain proper alignment of a sensor subassembly along the channel of the channel guide after motive force has been applied to the sensor subassembly.

Figure 7A:
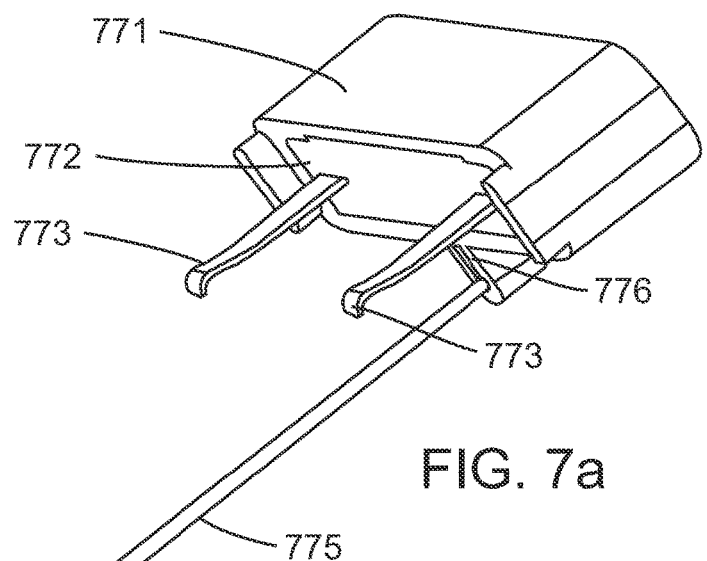
FIG. 7a illustrates a sensor subassembly in accordance with various embodiments.
Figure 7C:
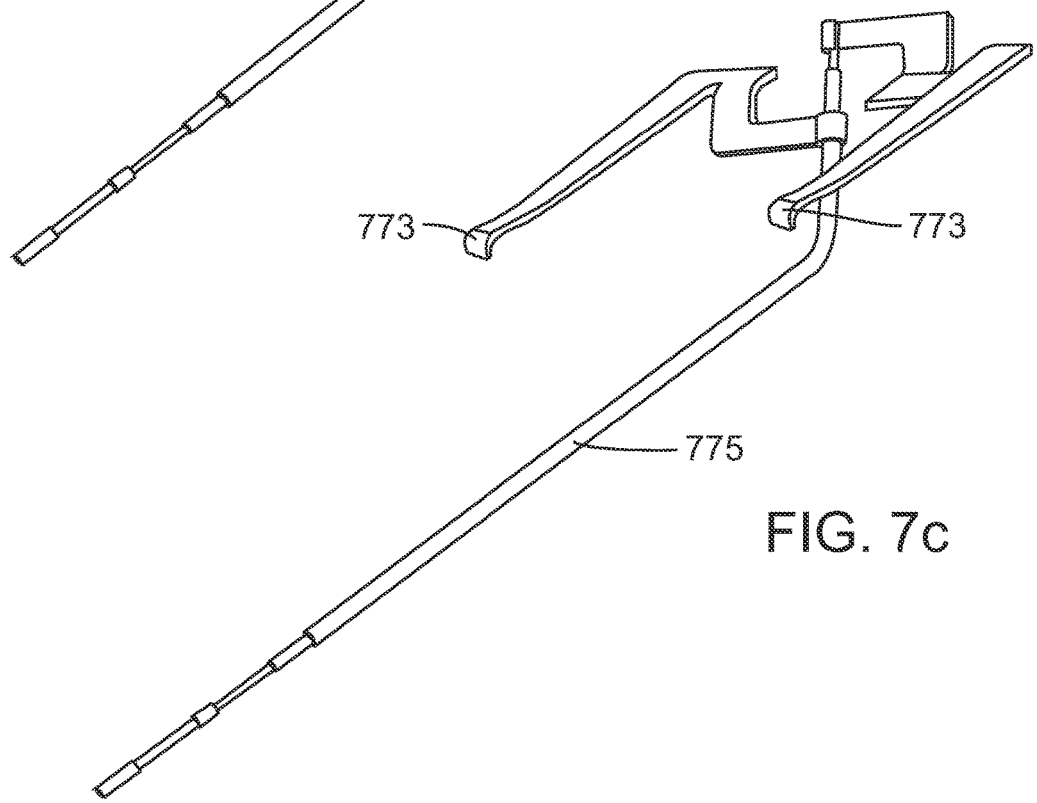
FIG. 7c illustrates a perspective view of a sensor coupled with sensor contacts and sensor contact spring elements in accordance with various embodiments.
Figure 7B:
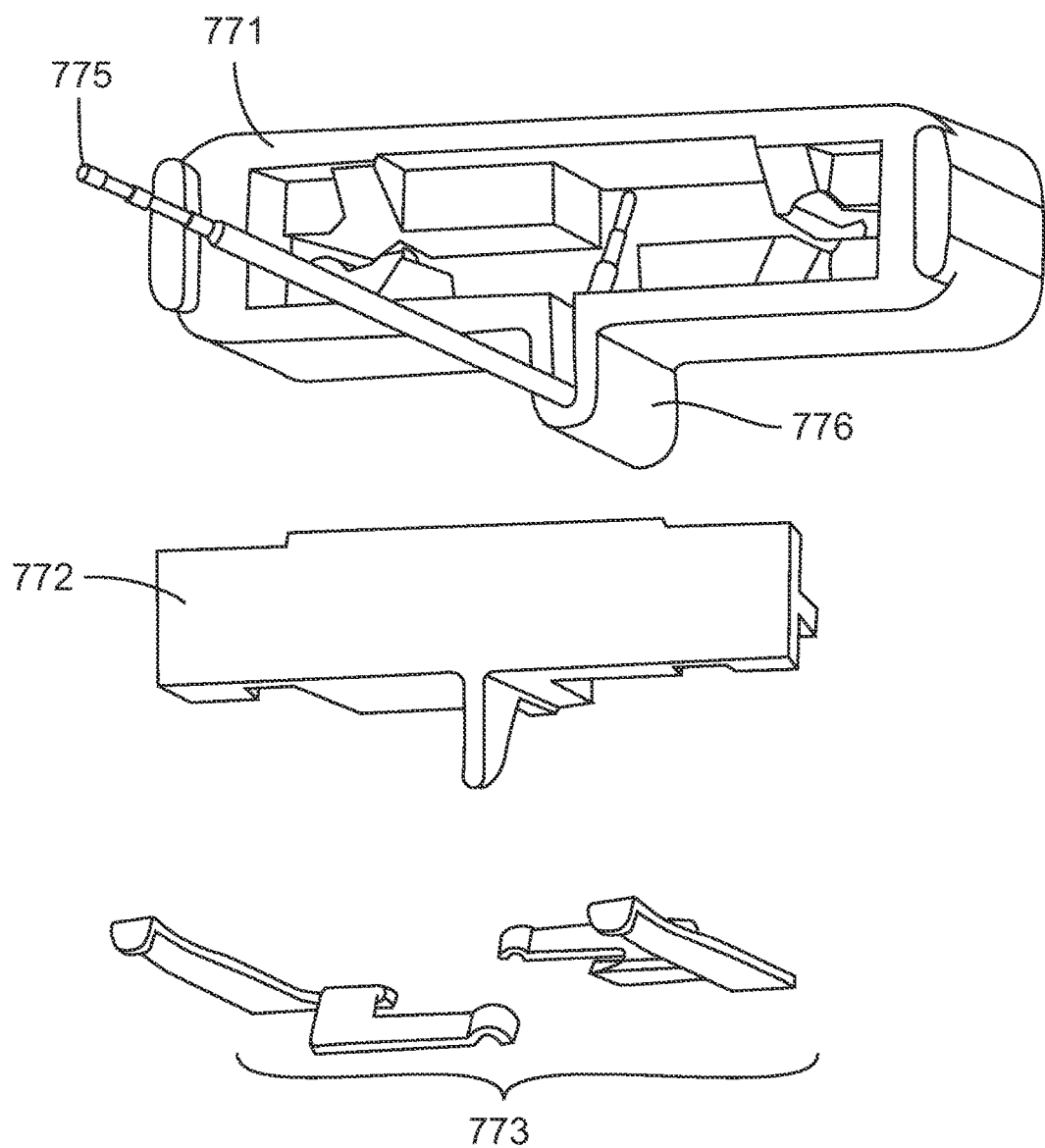
FIG. 7b illustrates a partially exploded view of a sensor subassembly in accordance with various embodiments.
Figure 7D:
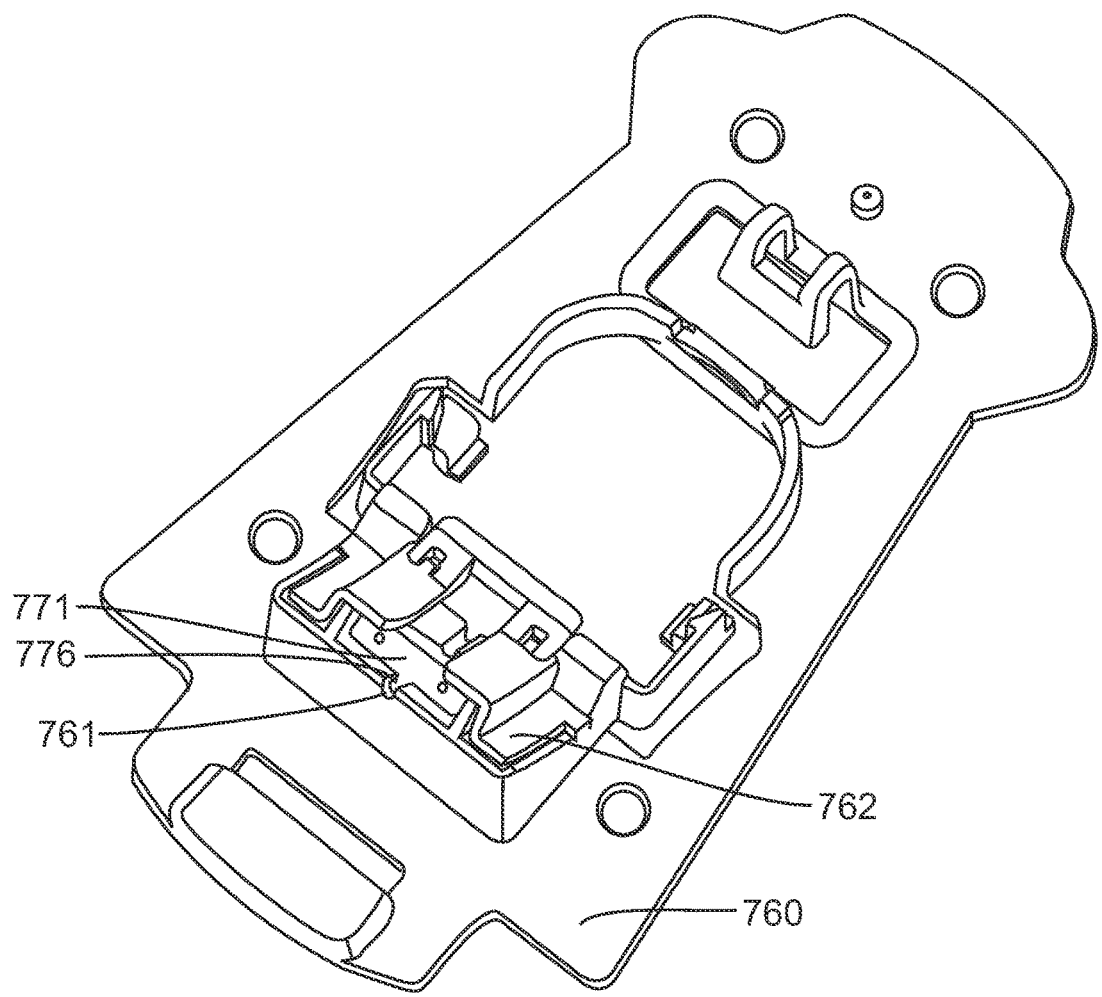
FIG. 7d illustrates a sensor subassembly housing in position for sensor insertion within a channel guide assembly in accordance with various embodiments.

FIGS. 7a-7d illustrate embodiments of a sensor subassembly. FIG. 7b illustrates a partially exploded view of a sensor subassembly. FIG. 7d illustrates a sensor subassembly housing in position for sensor insertion within a channel guide assembly.

Embodiments of a sensor assembly such as those shown in FIGS. 7a-7d may include a housing 771, encapsulant 772, sensor contacts 773, and/or a sensor 775. A sensor 775 may be retained within a housing 771 with encapsulant 772. Housing 771 may be shaped, or may include one or more protrusions and/or surface features, to allow one or more surfaces of housing 771 to mate with a channel guide 760 and/or channel guide cover 762. For example, a housing may include a feature such as keel 776 to retain/accommodate a sensor and/or to be retained within a groove or channel of a channel guide.

A sensor subassembly may include one or more sensor contacts configured to make electrical contact with a sensor assembly upon insertion of the sensor through/into skin.

In an embodiment, a sensor subassembly may be retained within a channel guide assembly until a motive force is applied, moving the sensor subassembly downward and causing both sensor insertion and electrical contact between the sensor subassembly and a sensor assembly mechanically coupled to and/or retained within an aperture of a channel guide.

Figure 8A:
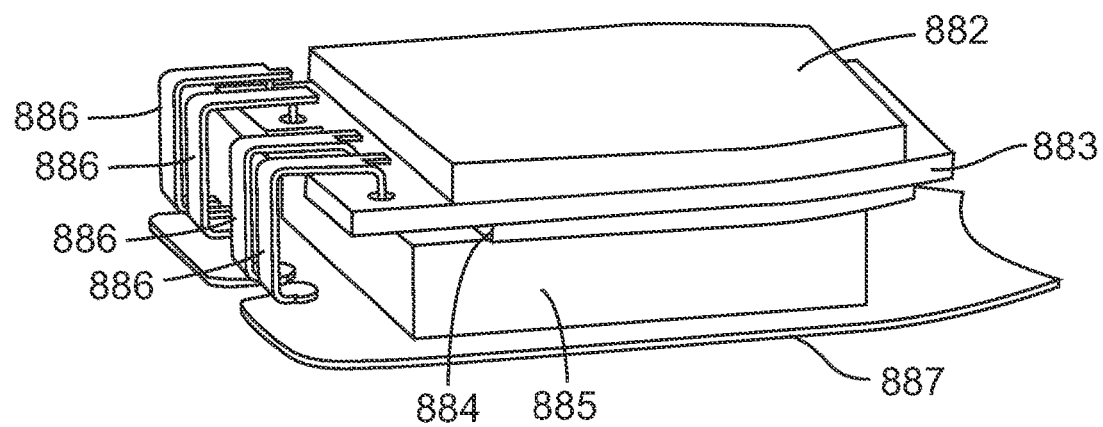
FIGS. 8a-8b illustrate a reusable sensor assembly (RSA) that may be mated to a disposable sensor assembly (DSA) in accordance with various embodiments.
Figure 8B:
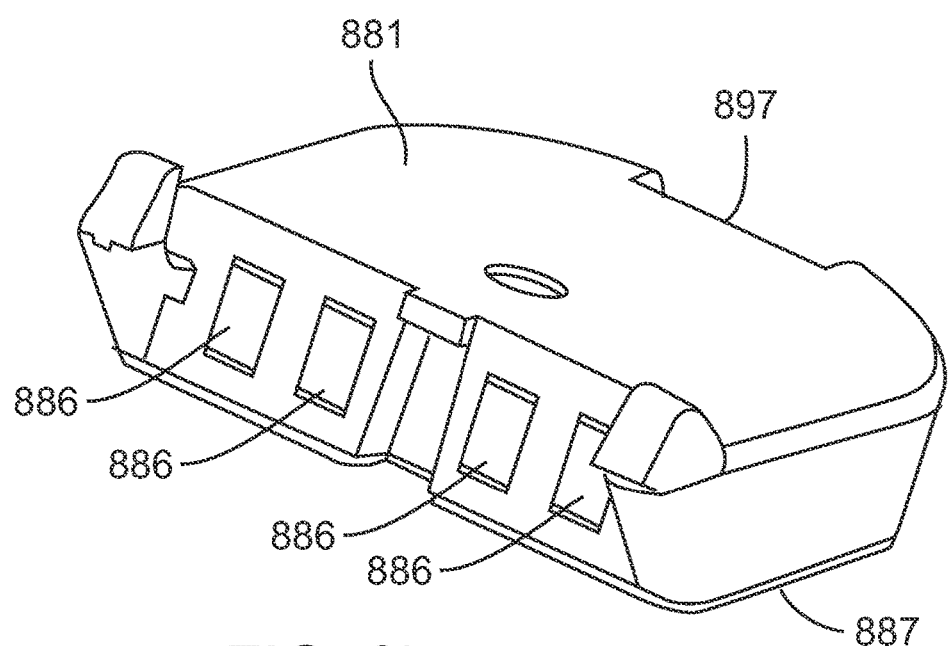

FIGS. 8a-8b illustrate a reusable sensor assembly (RSA) that may be mated to a disposable sensor assembly (DSA) in accordance with various embodiments. A RSA may comprise a housing 881 with one or more surface features configured to allow reversible coupling and/or locking of the RSA to a DSA or other component, such as latch receptacle 897. A RSA may further comprise electronic circuitry and/or a power source such as a battery. In the illustrated embodiment, a RSA includes a printed circuit board top layer 882, a printed circuit board layout 883, a printed circuit board bottom layer 884, a battery 885, four RSA sensor contacts 886, and a RSA cover 887. RSA sensor contacts may be coupled to RSA circuitry and may be configured for electrical communication with one or more sensor contacts of a sensor subassembly. A RSA housing may include one or more apertures through which the RSA sensor contacts are exposed. In some embodiments, a RSA may receive, store, and/or transmit signals representing analyte measurements from an individual.

Figure 9A:
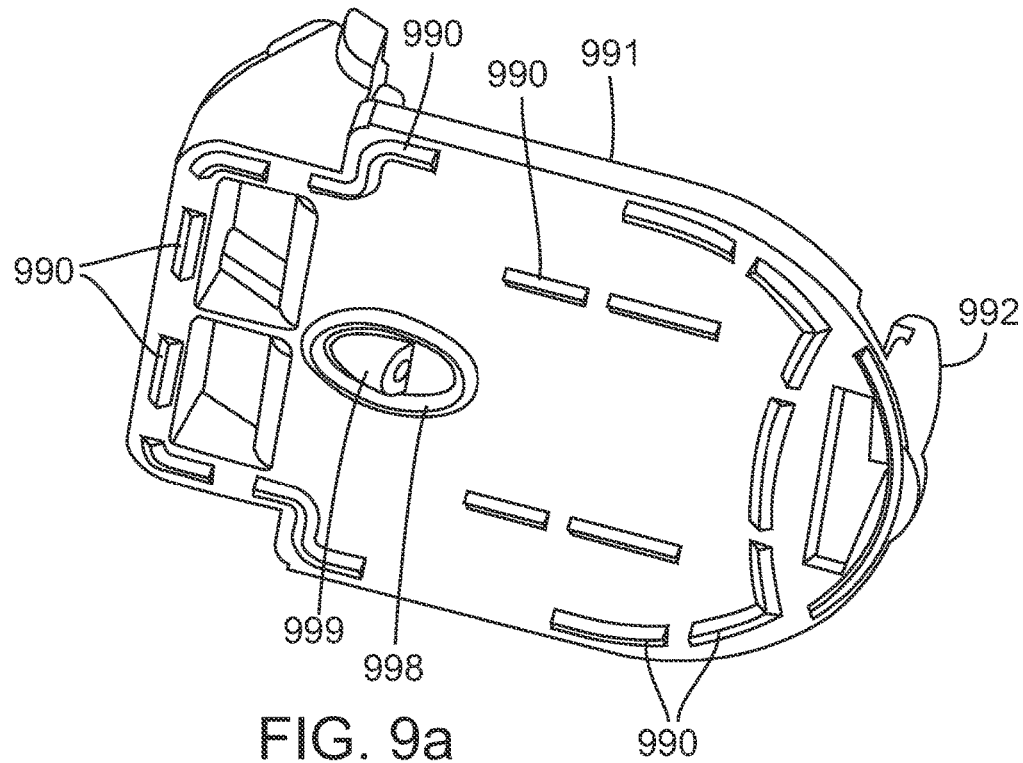
FIGS. 9a-9c illustrate a DSA which may be mated to a channel guide assembly and/or a RSA in accordance with various embodiments.
Figure 9B:
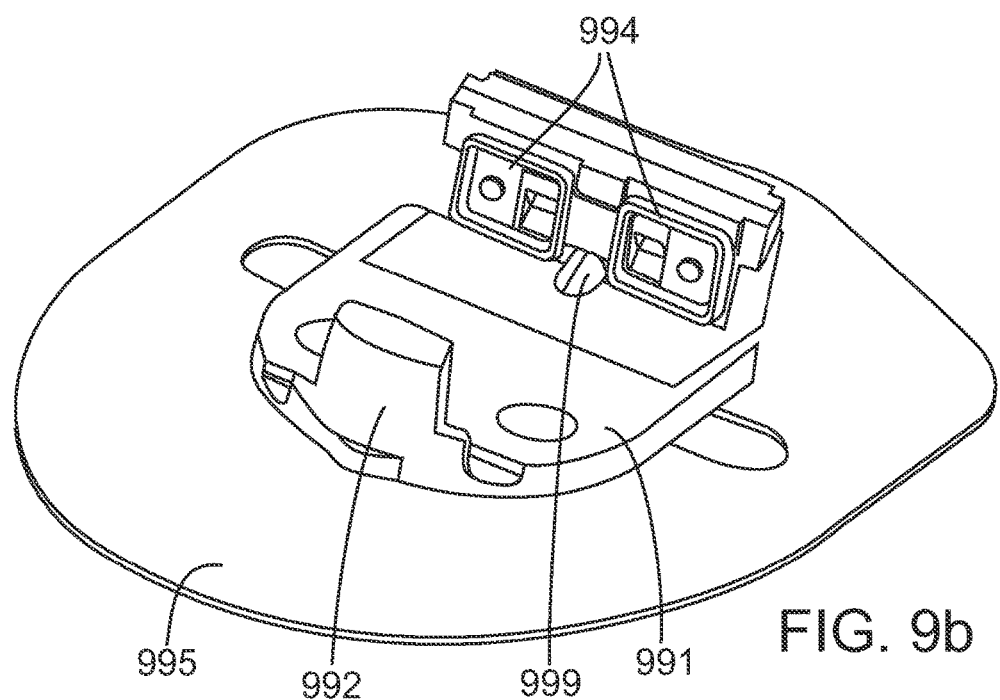
Figure 9C:
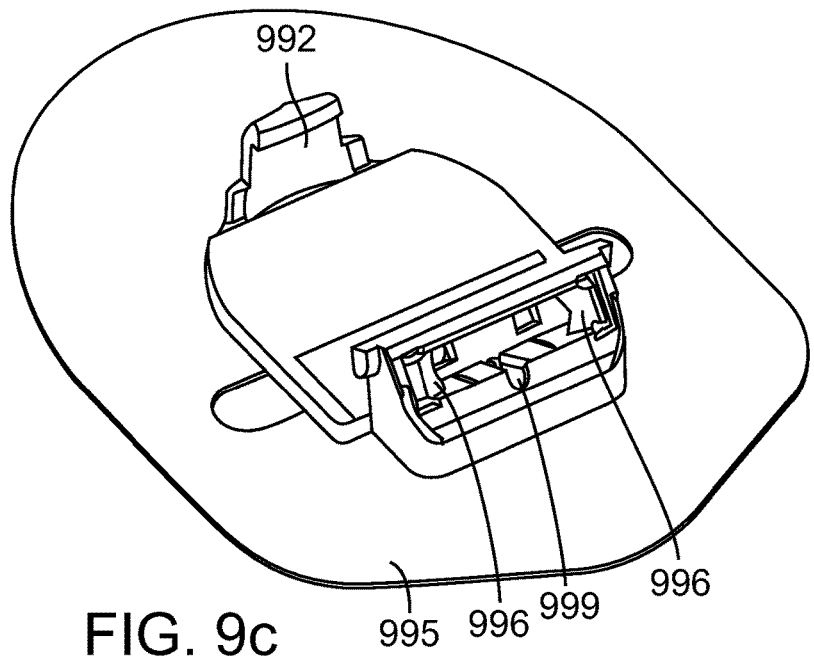
Figure 9D:
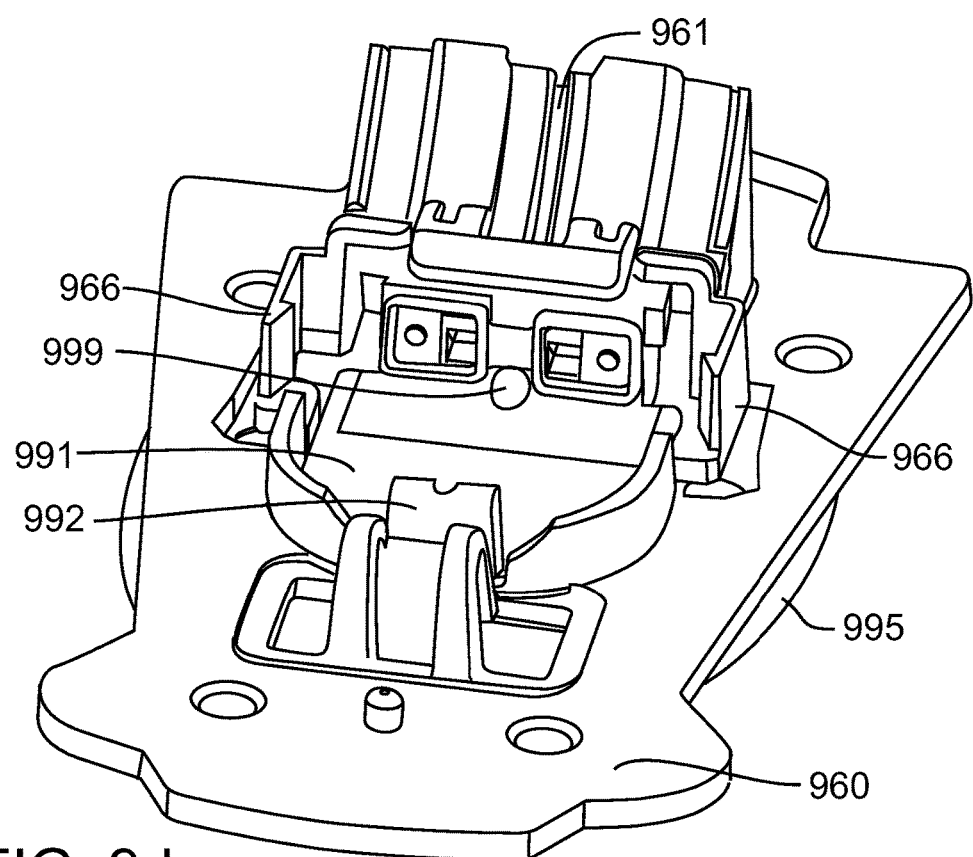
FIGS. 9d-9f illustrate a DSA coupled to a channel guide assembly and/or a RSA in accordance with various embodiments.
Figure 9E:
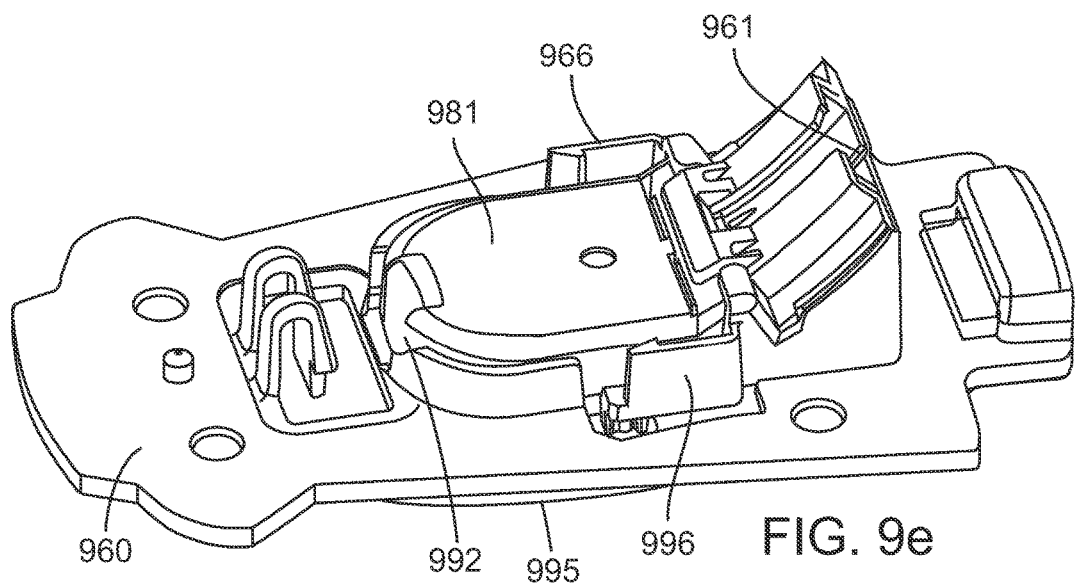
Figure 9F:
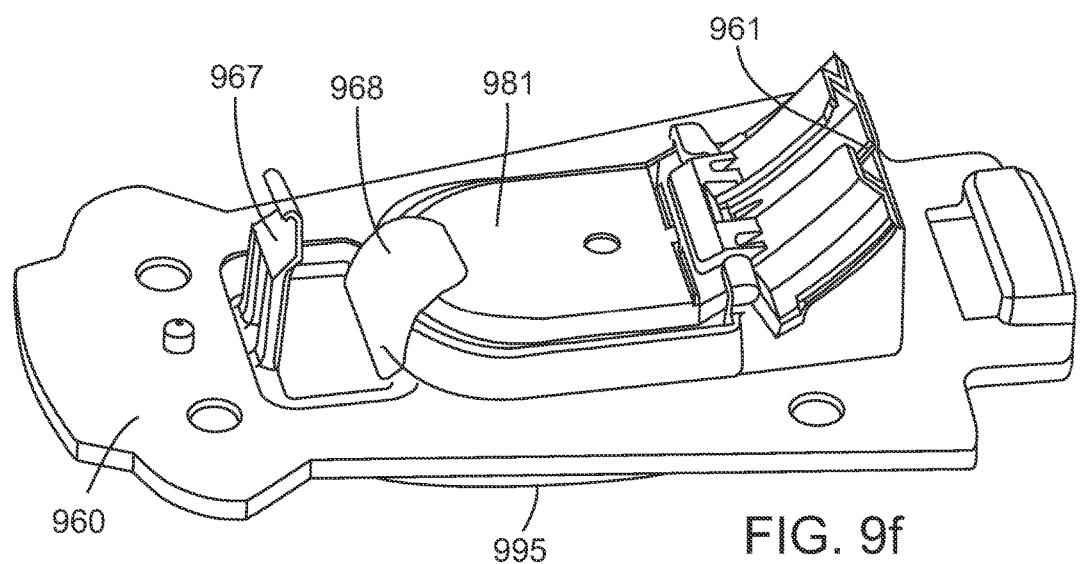

FIGS. 9a-9c illustrate a DSA which may be mated to a channel guide assembly and/or a RSA in accordance with various embodiments. FIGS. 9d-9f illustrate a DSA coupled to a channel guide assembly and/or a RSA. A DSA may comprise an adhesive patch 995, a housing 991, one or more gaskets 994, sensor subassembly retainer clips 996, a sensor channel 999, a latch member 992, and/or a skin contact member 998. As shown in FIG. 9a, a DSA/housing may include raised surface features 990, a skin contact element 998 and the terminal portion of channel 999. Latch member 992 may cause retention and/or locking of a RSA to a DSA until engaged directly or indirectly by a release mechanism and/or a user. A skin contact element 998 and/or other bottom surface features of a DSA may operate to stretch and/or pull skin taut in preparation for sensor insertion. In an embodiment, skin contact element 998 may comprise one or more sections joined to the bottom surface of a DSA, and the one or more sections may be configured to splay outward in response to pressure (e.g. pressing skin contact element against skin causes skin contact element to splay outward, stretching skin).

An adhesive patch may be made of any suitable material such as plastic, natural fibers, an elastomer, a polymer, silicone, etc. An adhesive patch may have one or more antimicrobial characteristics and/or include an antimicrobial substance. In some embodiments, an adhesive patch may be at least somewhat gas/liquid permeable.

One or more surface features 990 may be included to facilitate manufacturing and may be absent in a DSA provided to an end user. For example, in some embodiments one or more surface features 990 may function as energy directors for ultrasonic welding of an adhesive patch to the bottom of the DSA, and may be at least partially flattened during/after welding. Surface features 990 may also operate to couple to an adhesive patch 995, to allow airflow and/or moisture evaporation around skin under the DSA while the DSA is retained on the skin, and/or to accommodate surface features of other components of a sensor insertion system. While surface features 990 are shown in FIG. 9a as being positioned around the edges of the bottom surface of a DSA, embodiments vary as to the number and positions of bottom surface features. In embodiments, bottom surface features may be arranged in rows, circles, grids, or other suitable patterns. Some embodiments may lack bottom surface features and/or a skin contact element.

A DSA may be provided to secure a RSA as part of a sensor assembly and/or to facilitate electrical communication between a RSA and a sensor/sensor subassembly. A DSA may be adapted to remain on the skin of a user after sensor insertion. Adhesive patch 995 may secure the DSA to the skin of a user. While adhesive patch 995 is shown positioned on a bottom surface of a DSA in FIGS. 9b and 9c, in other embodiments an adhesive patch may be supplied separately for placement over the top surface of a DSA and RSA after sensor insertion. Channel 999 may be provided within a DSA at various angles to the skin, and may be configured to accommodate a portion of a sensor before/after sensor insertion.

A DSA may be provided with one or more gaskets 994 to provide a seal between a RSA and the DSA housing, as shown in FIG. 9b. A DSA may be configured to mate to a channel guide assembly for sensor insertion. Sensor retainer clips 996 may be provided to retain a sensor subassembly housing or other component of a sensor subassembly. Retention elements such as sensor retainer clips may be retained within a recess configured to accommodate the shape of a sensor subassembly such that motive force applied to the sensor subassembly drives the sensor subassembly down a surface of a channel guide and into the recess to engage the retention elements/retainer clips. The retention elements/retainer clips may hold the sensor subassembly to the sensor assembly after insertion of a sensor, maintaining the sensor and sensor subassembly in electrical contact with a RSA while coupled to the DSA.

To accommodate a sensor subassembly and/or sensor, a DSA may be configured with a groove or other feature within a recess, with the groove/feature corresponding to a protrusion or other surface element of the sensor subassembly. In the illustrated embodiment, a DSA is shown with a recess comprising a groove/channel to accommodate a sensor/subassembly.

FIGS. 9d-9f show a DSA mechanically coupled to a channel guide assembly. A DSA may be configured to snap into place within an aperture or other feature of a channel guide 960. Retention members 966 may, when pushed by a release member/mechanism, uncouple the sensor assembly (including a DSA and a RSA) from channel guide 960. A channel guide groove 961 may be matched to a sensor channel 999 such that the components form a continuous channel when mechanically coupled and/or releasably locked in contact.

In operation, a DSA may be mechanically coupled first to RSA 981 before coupling to channel guide 960. In some embodiments, a DSA may be mechanically coupled to channel guide 960 and may then be coupled to RSA 981. A motive force may be applied by a SIT mechanically coupled to the channel guide assembly, striking/propelling a sensor subassembly with sufficient force to drive the sensor subassembly housing into a recess or other surface feature of the DSA, where retention clips may securely couple the sensor subassembly housing to the DSA. Apertures in the DSA may be configured to accommodate sensor contacts of the sensor subassembly, which may pass through the apertures to contact RSA contact elements. The DSA and RSA may be retained on the skin until the useful life of the inserted sensor has passed, at which time the DSA may be discarded and the RSA re-used with a new DSA and other components of a sensor insertion device.

In some embodiments, as shown in FIG. 9f, a channel guide may include one or more features configured to interact with a release element to release the channel guide from a sensor assembly or a SIT. In an embodiment, a feature of a channel guide may be configured to retain a sensor assembly/SIT prior to sensor insertion and also to release a sensor assembly/SIT after sensor insertion. In FIG. 9f, a release element 967 of a sensor assembly is configured to engage a component of a SIT (e.g. a surface of a release element/button) prior to sensor insertion, and a release element 968 is configured to engage a sensor assembly prior to sensor insertion. In the illustrated embodiment, release element 967 is configured to allow mechanical coupling of release element 967 to a release member such as a release button (see FIG. 5c, showing a cutaway side view of a SIT with release button 544). Release element 967 may be flexible or semi-flexible and may be constructed of any suitable material, such as plastic and/or an elastomer. Pressing the release button may push the release element 967 backward, causing the release element 967 to disengage from the release button. Alternatively, pressing the release button may force the release element 967 backward and downward to press against the release element 968, causing release element 968 to press downward against the sensor assembly with sufficient force to disengage the sensor assembly from the channel guide. In an embodiment, release element 967 may disengage from the release button after the sensor assembly has been disengaged from the channel guide. In another embodiment, release element 967 may first disengage from the release button, uncoupling the SIT from the remaining components, and release element 968 may then be manually pressed to disengage the channel guide from the sensor assembly.

In embodiments, a release element and/or retention element may be spring-loaded, elastomeric, flexible, and/or configured to apply tension to one or more other components/features. A release/retention element may be formed as an integral feature of a component (e.g. a channel guide, DSA, RSA, sensor assembly component or SIT component) or may be added to a component. In some embodiments, a release/retention element may be configured to be used for only one release, while in other embodiments a release/retention element may be configured for multiple releases.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A sensor insertion tool for inserting a sensor through intact skin without a cannula or trocar, comprising:
   a channel guide assembly, comprising
      a channel guide, and
      a channel guide cover, wherein the channel guide and the channel guide cover together form a channel guide assembly channel;
   a motive force assembly to store and release energy, comprising
      a motive force member,
      a hammer channel separate from and non-contiguous with the channel guide assembly channel, and having a curved portion,
      a hammer extending through the channel guide cover into the channel guide assembly channel, and
      a hammer pin coupled to and extending transverse from the hammer, the hammer pin configured to extend from the hammer into the hammer channel and move along the curved portion of the hammer channel to guide the hammer to strike a sensor subassembly positioned within the channel guide assembly channel;
   a cocking assembly coupled to the motive force assembly to load energy into the motive force assembly; and
   a trigger assembly having a trigger member coupled to the motive force assembly to release stored energy in response to actuation of the trigger member.

2. The sensor insertion tool of claim 1, wherein the sensor insertion tool is disposable.

3. The sensor insertion tool of claim 1, wherein the channel guide assembly is permanently coupled to the motive force assembly.

4. A sensor insertion tool for inserting a sensor through intact skin without a cannula or trocar, comprising:
   a motive force assembly comprising
      a motive force member,
      a curved track,
      a hammer, and
      a hammer pin coupled to and extending transverse from the hammer into the curved track, the hammer pin configured to move along a curved portion of the curved track to guide the hammer to strike a sensor subassembly within a channel guide assembly channel separate from and non-contiguous with the curved track, the channel guide assembly comprising a channel guide, and a channel guide cover that together form the channel guide assembly channel;

a cocking assembly coupled to the motive force assembly to load energy into the motive force assembly;

a trigger assembly coupled to the motive force assembly to release the energy in response to actuation of the trigger assembly; and a retention element that couples the sensor subassembly to the channel guide assembly.

5. The sensor insertion tool of claim 4, wherein the motive force member comprises one or more springs.

6. The sensor insertion tool of claim 4, further comprising a release member to engage a component of the channel guide assembly to retain the sensor subassembly, the actuation of the release member adapted to cause an uncoupling of the sensor subassembly from the channel guide assembly.

7. The sensor insertion tool of claim 4, further comprising an elongated housing.

8. The sensor insertion tool of claim 4, further including the channel guide assembly.

9. The sensor insertion tool of claim 8, wherein the channel guide assembly is permanently coupled to a component of the sensor insertion tool.

10. The sensor assembly insertion tool of claim 4, wherein the sensor assembly insertion tool is a single use device.

11. The sensor insertion tool of claim 1, wherein the channel guide assembly comprises:

an elongated housing to reversibly mechanically lock in contact with the sensor subassembly and having a vertically protruding interior region and an aperture; and a channel defined by the vertically protruding interior region of the housing, the channel providing a passage through the channel guide assembly, said channel to accommodate the sensor subassembly.

12. The sensor insertion tool of claim 11, wherein the channel guide assembly reversibly mechanically locks to the sensor subassembly prior to sensor insertion.

13. The sensor insertion tool of claim 12, wherein the channel guide assembly is releasable from the sensor subassembly by actuation of a release member of the channel guide or the sensor insertion tool.

14. The sensor insertion tool of claim 11, wherein the elongated housing comprises a release element that unlocks the analyte sensor assembly from the channel guide assembly.

15. The sensor insertion tool of claim 7, wherein the elongated housing comprises a cocking indicator.

* * * * *